(12) United States Patent
Damestani et al.

(10) Patent No.: US 11,385,140 B2
(45) Date of Patent: Jul. 12, 2022

(54) TESTING ASSEMBLIES AND TESTING METHODS FOR DRUG DELIVERY DEVICES

(71) Applicant: AMGEN INC., Thousand Oaks, CA (US)

(72) Inventors: Yasaman Damestani, Thousand Oaks, CA (US); Bryton De Guia, Newbury Park, CA (US); Martin Hering, Camarillo, CA (US); Matthew Wayne Janke, Simi Valley, CA (US); Jerome Olivas, Thousand Oaks, CA (US); David Plescia, Concord Township, OH (US); Brendan Smyth, Camarillo, CA (US); Guojie Song, Moorpark, CA (US)

(73) Assignee: AMGEN INC., Thousand Oaks, CA (US)

( * ) Notice: Subject to any disclaimer, the term of this patent is extended or adjusted under 35 U.S.C. 154(b) by 952 days.

(21) Appl. No.: 16/151,720

(22) Filed: Oct. 4, 2018

(65) Prior Publication Data
US 2019/0247579 A1    Aug. 15, 2019

Related U.S. Application Data

(60) Provisional application No. 62/569,254, filed on Oct. 6, 2017.

(51) Int. Cl.
*G01M 99/00*    (2011.01)
*G01F 25/00*    (2022.01)
(Continued)

(52) U.S. Cl.
CPC ............ *G01M 99/008* (2013.01); *A61M 5/00* (2013.01); *F04B 51/00* (2013.01);
(Continued)

(58) Field of Classification Search
CPC ... G01M 99/008; G01M 99/005; G01L 25/00; A61M 5/00; A61M 2209/02;
(Continued)

(56) References Cited

U.S. PATENT DOCUMENTS 5,468,233 A * 11/1995 Schraga ............. A61M 5/1782
141/27
6,068,615 A * 5/2000 Brown ................ A61M 5/1782
604/207

(Continued)

*Primary Examiner* — Christopher P McAndrew
*Assistant Examiner* — Byung Ro Lee
(74) *Attorney, Agent, or Firm* — Marshall, Gerstein & Borun LLP

(57) ABSTRACT

A testing assembly for a drug delivery device is disclosed. The testing assembly can include a pressure vessel having a sealed pressure chamber that is configured to be pressurized to a predetermined pressure. The pressure vessel further defines an injection opening extending from an exterior thereof to the pressure chamber. A pierceable barrier extends over and seals the injection opening. The testing assembly further includes a measurement device disposed within the pressure chamber and a container aligned with the injection opening, such that the container is configured to collect a dose of a drug delivered via a drug delivery device through the pierceable barrier and the measurement device is configured to measure the dose of the drug.

20 Claims, 12 Drawing Sheets

(51) Int. Cl.
*F04B 51/00* (2006.01)
*A61M 5/00* (2006.01)
*G01L 25/00* (2006.01)
*A61M 5/20* (2006.01)
*B29L 31/00* (2006.01)
*A61M 5/31* (2006.01)
*A61M 5/142* (2006.01)

(52) U.S. Cl.
CPC .......... *G01F 25/0084* (2013.01); *G01L 25/00* (2013.01); *G01M 99/005* (2013.01); *A61M 5/14248* (2013.01); *A61M 5/20* (2013.01); *A61M 5/3129* (2013.01); *A61M 2005/3142* (2013.01); *A61M 2205/3331* (2013.01); *A61M 2205/70* (2013.01); *A61M 2209/02* (2013.01); *B29L 2031/7544* (2013.01)

(58) Field of Classification Search
CPC ...... A61M 5/14248; A61M 2205/3331; A61M 2205/70; A61M 5/20; A61M 2005/3142; A61M 5/3129; F04B 51/00; G01F 25/0084; B29L 2031/7544
USPC ....................................................... 73/865.9
See application file for complete search history.

(56) References Cited

U.S. PATENT DOCUMENTS

| | | | |
|---|---|---|---|
| 6,689,108 B2* | 2/2004 | Lavi | A61M 5/19 604/131 |
| 10,814,062 B2* | 10/2020 | Gyory | A61M 5/14212 |
| 2015/0057613 A1* | 2/2015 | Clemente | A61M 5/14248 604/148 |
| 2015/0133855 A1* | 5/2015 | Smith | A61M 5/145 604/67 |
| 2015/0290078 A1* | 10/2015 | Li | A61J 1/1406 206/222 |

* cited by examiner

TESTING ASSEMBLIES AND TESTING METHODS FOR DRUG DELIVERY DEVICES

CROSS-REFERENCE TO RELATED APPLICATIONS

Priority is claimed to U.S. Provisional Application No. 62/569,254, filed on Oct. 6, 2017, the entire contents of which are incorporated herein by reference.

FIELD OF THE DISCLOSURE

The present disclosure generally concerns drug delivery devices and, more particularly, the configuration of a testing assembly for drug delivery devices.

BACKGROUND

Drug delivery devices, such as injectors, may be used to deliver liquid drugs to a patient. Many drug delivery devices are configured to expel a drug stored within an internal reservoir through a needle, cannula, or other delivery structure into the patient. Such drug delivery devices may be subjected to a variety of performance tests to ensure that the devices are functioning properly. Due to different machines and setup requirements for the various tests, however, an individual drug delivery device is commonly used only once for a single particular test. This practice can be expensive, time-consuming, and wasteful.

The present disclosure sets forth testing assemblies for drug delivery devices and related methods of testing drug delivery devices embodying advantageous alternatives to conventional testing assemblies and methods, and that may address one or more of the challenges or needs mentioned herein, as well as provide other benefits and advantages.

SUMMARY

In some embodiments, a testing assembly for a drug delivery device is described herein that includes a pressure vessel having a pressure chamber configured to be pressurized to a predetermined pressure and defining an injection opening extending from an exterior thereof to the pressure chamber. The testing assembly can further include a pierceable barrier that extends over and seals the injection opening. A scale may be disposed within the pressure chamber and a container may be associated with the scale. The container can be aligned with the injection opening and be configured to collect a dose of drug delivered via delivery structure of a drug delivery device injected through the pierceable barrier. As such, the scale can be configured to measure a weight of the dose.

By one approach, the testing assembly can further include a device housing that is configured to securely retain the drug delivery device therein. The device housing can further be configured to couple to the pressure vessel to thereby orient the drug delivery device adjacent to the injection opening. By a further approach, the pressure vessel can further include a cap having the pierceable barrier therein, where the cap extends outwardly from adjacent portions of the exterior of the pressure vessel. The device housing can then include a recess having a shape complementary to the cap such that the device housing is configured to receive the cap within the recess thereof to mount the drug delivery device adjacent to the pierceable barrier.

By another approach, the testing assembly can further include an actuation force test assembly that is configured to engage an activation switch on the drug delivery device to determine a force required for actuation thereof. By a further approach, the actuation force test assembly can include a drive mechanism, a mount, and a force sensor, where the force sensor is coupled to a forward portion of the mount and the mount is configured to be driven by the drive mechanism so that the force sensor engages and actuates the activation switch of the drug delivery device.

By yet another approach, the testing assembly can further include a control circuit in communication with the scale and configured to determine a dispense time for the drug delivery device based at least in part on weight changes measured by the scale. By a further approach, the testing assembly can further include a sensor in communication with the control circuit that is configured to cause a timer to start upon actuation of an activation switch of the drug delivery device.

In several embodiments, a method for testing the operation of a drug delivery device having a delivery mechanism including delivery structure is described herein that includes pressurizing a pressure chamber within a pressure vessel to simulate back pressure created when subcutaneously delivering a drug. The method can then include operating the drug delivery device so that the delivery structure pierces a pierceable barrier extending over an injection opening of the pressure vessel. A dose of drug is then delivered through the delivery structure into the pressure chamber and collected within a container disposed within the pressure chamber. The method can then include measuring a weight of the dose using a scale.

By one approach, the method can further include determining a dispense time for the dose based at least in part on weight measurement changes.

By another approach, the method can further include determining an actuation force required to actuate an activation switch of the drug delivery device.

By yet another approach, the drug delivery device can be adhesively mounted to a base plate, and the method can further include determining a removal force required to remove the drug delivery device from the base plate.

BRIEF DESCRIPTION OF THE DRAWINGS

It is believed that the disclosure will be more fully understood from the following description taken in conjunction with the accompanying drawings. Some of the drawings may have been simplified by the omission of selected elements for the purpose of more clearly showing other elements. Such omissions of elements in some drawings are not necessarily indicative of the presence or absence of particular elements in any of the exemplary embodiments, except as may be explicitly delineated in the corresponding written description. Also, none of the drawings is necessarily to scale.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

In general terms, the present disclosure is concerned with the configuration of a testing assembly for and method of testing drug delivery devices. Various ones of the embodiments described herein can be utilized to test the functionality of suitable drug delivery devices, such as on-body injectors, autoinjectors, injection pens, and so forth.

On-Body Injector Disclosure

Figure 1:
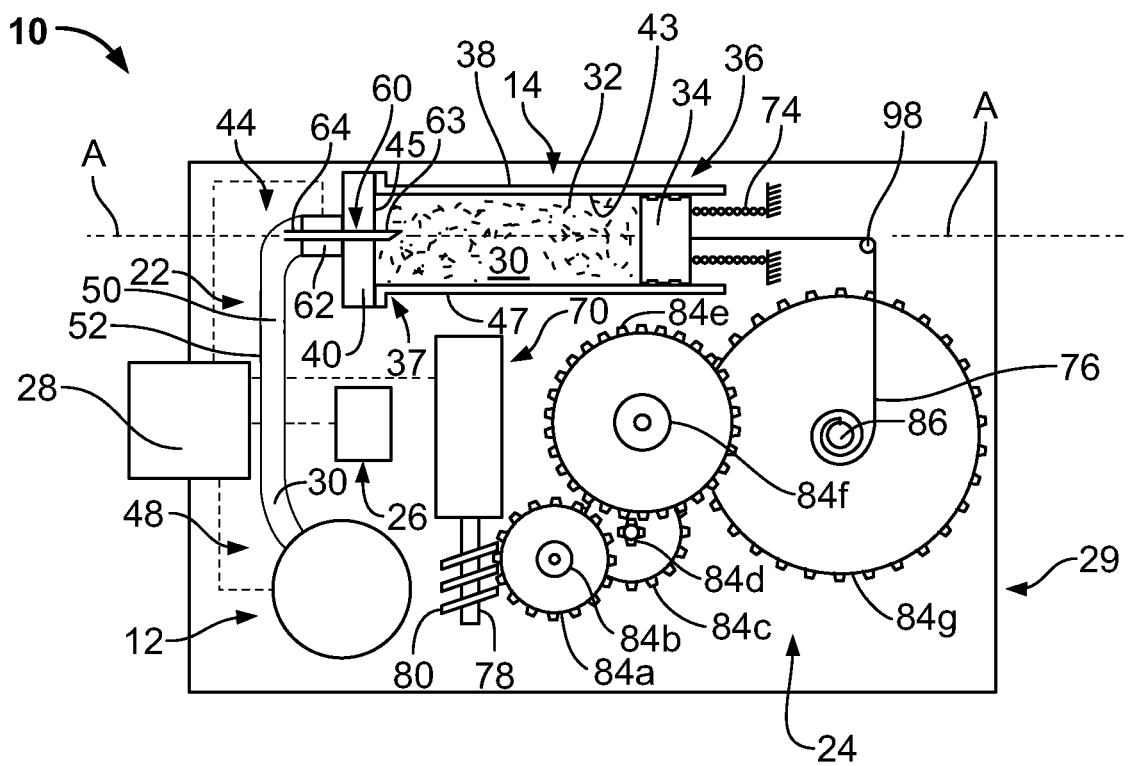
FIG. 1 is schematic top view of an embodiment of a drug delivery device in accordance with various embodiments.
Figure 2:
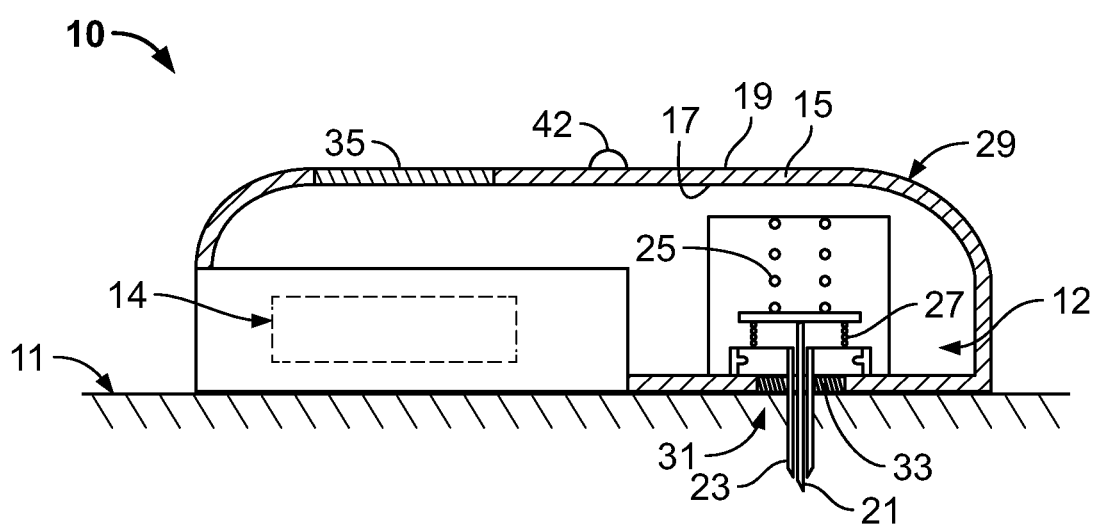
FIG. 2 is a schematic partial cross-sectional side view of the drug delivery device shown in FIG. 1 in accordance with various embodiments.

Before describing details of the testing assembly embodiments described herein, an example drug delivery is described with reference to FIGS. 1 and 2. FIGS. 1 and 2 are schematic illustrations of one embodiment of a drug delivery device 10 suitable for testing in the methods and assemblies in accordance with the present disclosure. The drug delivery device 10 may be operated to subcutaneously or transdermally deliver a drug to a patient. In the illustrated embodiment, the drug delivery device 10 is configured as a wearable drug delivery device, such as an on-body injector or an ambulatory infusion pump, which is releasably adhered to the patient's tissue 11 (e.g., the patient's skin). In other embodiments, such as that shown in FIG. 5, the drug delivery device 10 may be configured as a handheld injector 10', such as an autoinjector or injection pen, which is manually held against the patient's tissue 11 over the course of the injection. The drug delivery device 10 may be configured to automatically deliver a fixed or a patient/operator-settable dose of the drug over a controlled or selected period of time. Furthermore, the drug delivery device 10 may be intended for self-administration by the patient, or may be operated by a formally trained healthcare professional or other caregiver to administer the injection.

Generally, the drug delivery device 10 may include an insertion mechanism 12, a container 14, a fluid pathway assembly 22, a drive assembly 24, and a controller 26, each of which may be disposed within an interior enclosed space of a main housing 29. An input device 28 (e.g., a user-depressible button, touchscreen, microphone, etc.) may protrude through or otherwise be disposed at an exterior surface 19 of the main housing 29 and may be configured to initiate operation of the drug delivery device 10 by activating, via mechanical and/or electrical means (shown in dotted lines in FIG. 1), the insertion mechanism 12, the fluid pathway assembly 22, the drive assembly 24, the controller 26, and/or other mechanisms and/or electronics. In embodiments where the input device 28 is a button that is depressed or otherwise physically moved by a user or patient, the input device 28 may operate as an actuator that exerts a motive force needed to activate the insertion mechanism 12, the fluid pathway assembly 22, the drive assembly 24, the controller 26, and/or other mechanisms. In such embodiments, the input device 28 may be physically connected to, either directly or indirectly via a mechanical linkage, the insertion mechanism 12, the drive assembly 24, the fluid pathway assembly 22, and/or other mechanisms, such that manually depressing or otherwise interacting with the input device 28 supplies the motive force necessary to activate the insertion mechanism 12, the drive mechanism 24, the fluid pathway assembly 22, and/or other mechanisms. For example, in some embodiments, manually depressing the input device 28 may cause the fluid pathway assembly 22 to move towards the stationary container 14, or alternatively cause the container 14 to move towards the stationary fluid pathway assembly 22, and thereby cause a container access needle to penetrate through a seal member into a reservoir or interior volume of the container 14. Additionally or alternatively, depressing or otherwise interacting with the input device 28 may transmit an electrical and/or mechanical signal to the controller 26, which in turn may execute programmable instructions to control operation of the insertion mechanism 12, the drive assembly 24, and/or the fluid pathway assembly 22. In such embodiments, the controller 26 may include a processor (e.g., a microprocessor) and a non-transitory memory for storing the programmable instructions to be executed by the processor. Furthermore, in such embodiments, the drug delivery device 10 may include an internal actuator (e.g., an electric motor, a pneumatic or hydraulic pump, and/or a source of pressurized gas or liquid) which is separate from the input device 28 and which, in response to an electrical control signal received from the controller 26, exerts the motive force needed to activate the insertion mechanism 12, the drive assembly 24, the fluid pathway assembly 22, and/or other mechanisms. One example of such an internal actuator is the rotational power source of the drive assembly 24, which is described in more detail below.

Referring to FIG. 2, the main housing 29 may include a wall 15 having an interior surface 17 and an exterior surface 19. The wall 15 may be a single unitary structure or made of multiple distinct structures interconnected with each other. The interior surface 17 of the wall 15 may define an enclosed space in which the insertion mechanism 12, the container 14, the fluid pathway assembly 22, the drive assembly 24, and the controller 26, and/or other mechanisms and/or components may be disposed. In some embodiments, the enclosed spaced may be sealed shut to define an enclosed clean space having, for example, a sterile or aseptic internal atmosphere. The exterior surface 19 of a bottom portion of the wall 15 may be releasably attachable to the patient's tissue 11. In some embodiments, this may be accomplished with a skin adhesive applied to or otherwise disposed at the exterior surface 19 of the bottom portion of the wall 15 of the main housing 29. In some embodiments, the skin adhesive may be part of an adhesive patch attached to the exterior surface 19 of the bottom portion of the wall 15 of the main housing 29. The exterior surface 19 of a top portion of the wall 15 may include one or more visual indicators 42 (e.g., lights, graphical displays, etc.) and/or a window 35 for viewing the container 14 and the drug 32 contained therein. The one or more visual indicators 42 may be used to communicate information to the user about the operational state of the drug delivery device 10 and/or the condition of the drug 32. An opening 31 may be formed in the bottom portion of the wall 15, and optionally a pierceable sterile barrier 33, such as a pierceable septum, may extend across the opening 31 to seal the interior of the main housing 29 prior to use. In some embodiments, the pierceable sterile barrier 33 may be omitted, and instead a removable sealing member (not illustrated) may cover and seal close the opening 31 prior to use.

More particularly with respect to the window 35, this element may be constructed of a transparent or semi-transparent material and generally aligned with the container 14, so as to allow a patient or user of the drug delivery device 10 to inspect the drug 32 within the container 14 and/or confirm dose completion. Suitable materials for constructing the window 35 include, but are not limited to, glass and/or plastic. The location of the window 35 on the exterior of the drug delivery device 10 may expose the drug 32 to ambient light including sunlight. Some drugs may be sensitive to certain wavelengths of light and undergo undesirable molecular changes when exposed to such wavelengths of light. For example, some drugs may be sensitive to wavelengths of light in the ultraviolet (UV) range, the visible range, and/or the infrared range. To protect drugs that are primarily sensitive to light in the UV range and/or the infrared range, a dark tint may be added to the window 35 and/or the window 35 may be dimensioned to cover a relatively small surface area of the main housing 29. For drugs that are primarily sensitive to light in the visible range, it may not be necessary to add a dark tint to the window 35 and/or shrink the size of the window 35. Instead, the window 35 may be constructed with a polarized filter. In some embodiments, the polarized filter may be a film or other coating that is applied to the window 35. In other embodiments, the polarized filter may be integrated directly into the material of window 35. The polarized filter may allow for viewing and inspection of the drug 32 within the container 14, while filtering out up to and including approximately (e.g., ±10%) 50% of light in the visible range. In some embodiments, the portion of visible light filtered out by the window 35 may fall in a range between approximately (e.g., ±10%) 0-50%, or 10-50%, or 20-50%, or 25-50%, or 0-40%, or 0-30%, or 0-25%, depending on the photosensitivity of the drug 32 and/or the eye strength of the patient population of the drug 32, among other considerations. Adding the polarized filter to the window 35, in lieu adding a dark tint to the window 35 and/or shrinking the size of the window 35, advantageously protects the drug 32 from light in the visible range without substantially compromising the ability of the patient or user of the drug delivery device 10 to inspect the drug 32 within the container 14.

After the bottom portion of the wall 15 of the main housing 29 is attached to the patient's tissue 11, the insertion mechanism 12 may be activated to move a subcutaneous delivery structure or member from a retracted position, where a pointed distal end of the subcutaneous delivery member is withdrawn within the main housing, to a deployed position, where the pointed distal end projects from the main housing 29 beyond the exterior surface 19 of the main housing 29. In the present embodiment, this may include the insertion mechanism 12 inserting a trocar 21 and a hollow cannula 23 surrounding the trocar 21 through the pierceable sterile barrier 33 and into the patient's tissue 11, as illustrated in FIG. 2. Immediately or shortly thereafter, the insertion mechanism 12 may automatically retract the trocar 21, leaving the distal end of the cannula 23 inside the patient for subcutaneous delivery of the drug 32. The trocar 21 may be solid and have a sharpened end for piercing the patient's skin 11. Furthermore, the trocar 21 may be made of a material that is more rigid than the cannula 23. In some embodiments, the trocar 21 may be made of metal, whereas the cannula 23 may be made of plastic or another polymer. The relative flexibility of the cannula 23 may allow it to be disposed subcutaneously within the patient's tissue 11 for a period of a time without causing pain or significant discomfort to the patient. The distal end of the cannula 23 may be sharpened to a point but may be more blunt than the distal end of the trocar 21. In other embodiments (not illustrated), the trocar 21 and cannula 23 may be omitted, and instead the insertion mechanism 12 may insert only a rigid, hollow needle into the patient's tissue 13 for subcutaneous delivery of the drug 32. Also, in one or more of these embodiments, the subcutaneous delivery member may have a longitudinal axis that is perpendicular to or otherwise non-parallel to the longitudinal axis A of the container 14.

Still referring to FIG. 2, the insertion mechanism 12 may include an insertion biasing member 25 and a retraction biasing member 27. Prior to activation of the insertion mechanism 12, each of the insertion biasing member 25 and the retraction biasing member 27 may be retained in an energized state. Upon activation of the insertion mechanism 12 via, e.g., the input device 28, the insertion biasing member 25 may release its stored energy to move the subcutaneous delivery member from the retracted position to the deployed position. In the illustrated embodiment, this involves moving the trocar 21 and the cannula 23 from a position where their distal ends are located within the main housing 29, to the position shown in FIG. 2. The retraction biasing member 27 may be retained in its energized state during the insertion procedure. Subsequent to the insertion procedure, the retraction biasing member 27 may release its stored energy to move the trocar 21 from the deployed position back to the retracted position, leaving the cannula 23 in the deployed position.

In the embodiment illustrated in FIG. 2, the insertion biasing member 25 and the retraction biasing member 27 are respective compression springs which are arranged concentrically with each other. Other power sources for the insertion biasing member 25 and/or the retraction biasing member 27 are also possible, including, for example, a torsion spring, an electric motor, a hydraulic or pneumatic pump, or a canister that releases a pressurized gas or a pressurized liquid to provide actuation energy. In some embodiments, the insertion biasing member 25 and the retraction biasing member 27 may be defined by a single electric motor which is operated in a forwards and a reverse direction to provide the insertion and retraction movements. Also, in some embodiments, the retraction biasing member 27 may be omitted.

Referring back to FIG. 1, the container 14, which in some contexts may be referred to as a primary container, may include a wall 38 with an interior surface 43 defining a reservoir 30 that is filled with the drug 32 and an exterior surface 47. In some embodiments, the reservoir 30 may be pre-filled with the drug 32 by a drug manufacturer prior to installation of the container 14 in the drug delivery device 10. In some embodiments, the container 14 may be rigidly connected to the housing 29 such that the container 14 cannot move relative to the housing; whereas, in other embodiments, the container 14 may be slidably connected to the main housing 29 such that the container 14 can move relative to the main housing 29 during operation of the drug delivery device 10. The container 14 may have an elongate, barrel-like or cylindrical shape extending along a longitudinal axis A. In embodiments where the drug delivery device 10 is configured as an on-body injector, the longitudinal axis A of the container 14 may be perpendicular or substantially perpendicular, or otherwise non-parallel, to a direction in which the insertion mechanism 12 inserts the subcutaneous delivery member such as the cannula 23 into the patient. This configuration may allow the on-body injector to have a generally planar, low-profile shape that can be worn by the patient without impeding the patient's movement. Initially, a stopper 34 or other piston member may be positioned in the reservoir 30 at a proximal end 36 of the container 14. The stopper 34 may sealingly and slidably engage the interior surface 43 of the wall 38 of the container 14, and may be movable relative to the wall 38 of the container 14 to expel the drug 32 from the container therein.

The volume of the drug 32 contained in the reservoir 30 prior to delivery may be: any volume in a range between approximately (e.g., ±10%) 0.5-20 mL, or any volume in a range between approximately (e.g., ±10%) 0.5-10 mL, or any volume in a range between approximately (e.g., ±10%) 1-10 mL, or any volume in a range between approximately (e.g., ±10%) 1-8 mL, or any volume in a range between approximately (e.g., ±10%) 1-5 mL, or any volume in a range between approximately (e.g., ±10%) 1-3.5 mL, or any volume in a range between approximately (e.g., ±10%) 1-3 mL, or any volume in a range between approximately (e.g., ±10%) 1-2.5 mL, or any volume in a range between approximately (e.g., ±10%) 1-2 mL, or any volume equal to or less than approximately (e.g., ±10%) 4 mL, or any volume equal to or less than approximately (e.g., ±10%) 3.5 mL, or any volume equal to or less than approximately (e.g., ±10%) 3 mL, or any volume equal to or less than approximately (e.g., ±10%) 2.5 mL, or any volume equal to or less than approximately (e.g., ±10%) 2 mL, or any volume equal to or less than approximately (e.g., ±10%) 1.5 mL, or any volume equal to or less than approximately (e.g., ±10%) 1 mL. The reservoir 30 may be completely or partially filled with the drug 32. The drug 32 may be one or more of the drugs described below, such as, for example, a granulocyte colony-stimulating factor (G-CSF), a PCSK9 (Proprotein Convertase Subtilisin/Kexin Type 9) specific antibody, a sclerostin antibody, or a calcitonin gene-related peptide (CGRP) antibody.

During operation of the drug delivery device 10, the drive assembly 24 may push the stopper 34 along the longitudinal axis A through the reservoir 30 from the proximal end 36 of the container 14 to a distal end 37 of the container 14 in order to expel the drug 32. As described below in more detail, the drive assembly 24 may include a rotational power source, a gear module configured to convert the rotational speed and/or torque of the rotational movement output by the rotational power source, a stopper biasing member initially retained in an energized state and configured to axially expand to move the stopper through the reservoir 30, and a tether configured to restrain or otherwise regulate the expansion of the stopper biasing member.

At the distal end 37 of the container 14, an opening 45 may be formed in the wall 38. At least prior to operation of the drug delivery device 10, the opening 45 may be covered and sealed closed by a seal member 40, such as a pierceable septum, connected to the distal end 37 of the container 14. A proximal end surface of the seal member 40 and the interior surface 43 of the wall 38 of the container 14 may define the reservoir 30. Additionally, in some embodiments, a distal end surface of the stopper 34 may define the reservoir 30.

Generally, the seal member 40 may be configured to selectively permit access to the reservoir 30. During operation of the drug delivery device 10, the seal member 40 may be physically altered (e.g., pierced) to permit fluid communication with the drug 32 in the reservoir 30. In some embodiments, the seal member 40 may be constructed of a flexible or elastically deformable material such as rubber, for example, which is capable of being penetrated or pierced by a sharpened end or point 63 of a container access needle 60 of the fluid pathway assembly 22. In some embodiments, the seal member 40 may be clamped or otherwise secured to the distal end surface of the wall 38 of the container 14 by a fastener (e.g., a crimp ring) and/or adhered directly to the distal end surface of the wall 38 of the container 14.

Still referring to FIG. 1, the fluid pathway assembly 22 may be configured to establish fluid communication between the container 14 and the insertion mechanism 12 via a sterile fluid flow path during operation of the drug delivery device 10. Prior to use of the drug delivery device 10, the fluid pathway assembly 22 may not be in fluid communication with the container 14. During setup of the drug delivery device 10, or during the initial stages of operation of the drug delivery device 10 prior to drug delivery, the user may manually, or the drug delivery device 10 may automatically, enable, connect, or open the necessary connections to establish fluid communication between the container 14 and the fluid pathway assembly 22. Subsequently, the drive assembly 24 may move the stopper 34 in the distal direction relative to the wall 38 of the container 14 to force the drug 32 stored in the container 14 through the sterile fluid flow path of the fluid pathway assembly 22 and into the cannula 23 or needle or other delivery member of the insertion mechanism 12 for subcutaneous delivery to the patient.

The fluid pathway assembly 22 may include a first end 44 connected to the container 14, a second end 48 connected to the insertion mechanism 12, and a fluid passage 50 extending between the first end 44 and the second end 48. The fluid passage 50 may be sterilized, and may be partially or entirely made of a flexible tubing 52.

Still referring to FIG. 1, the first end 44 of the fluid pathway assembly 22 may include the container access needle 60 and a connection hub or mounting member 62. The container access needle 60 may have a sharpened end or point 63, corresponding to a proximal end of the container access needle 60, and a distal end 64 in fluid communication with the fluid passage 50. The mounting member 62 may cover a length of the distal end 64 of the container access needle 60 and connect the distal end 64 of the container access needle 60 to the flexible tubing 52.

Where appropriate, any of the above-described sub-assemblies, mechanisms, components, features, functionalities, methods of manufacture, methods of use, and other aspects of the drug delivery device 10 may be replaced with and/or combined with any of the sub-assemblies, mechanisms, components, features, functionalities, methods of manufacture, methods of use, and other aspects of the drug delivery devices described in some or all of the following documents, each of which is hereby incorporated by reference in its entirety for all purposes: U.S. Pat. No. 9,061,097; U.S. Patent Application Publication No. 2017/0124284; U.S. Patent Application Publication No. 2017/0119969; U.S. Patent Application Publication No. 2017/0098058; U.S. Patent Application Publication No. 2017/0124285; U.S. Patent Application Publication No. 2017/0103186; U.S. Provisional Patent Application No. 62/460,501 entitled "INSERTION MECHANISM FOR DRUG DELIVERY DEVICE"; U.S. Provisional Patent Application No. 62/469,226 entitled "INSERTION MECHANISM FOR DRUG DELIVERY DEVICE"; U.S. Provisional Patent Application No. 62/468,190 entitled "INSERTION MECHANISM AND METHOD OF INSERTING A NEEDLE OF A DRUG DELIVERY DEVICE"; U.S. Provisional Patent Application No. 62/460,559 entitled "DRUG DELIVERY DEVICE WITH STERILE FLUID FLOWPATH AND RELATED METHOD OF ASSEMBLY"; U.S. Provisional Patent Application No. 62/294,842 entitled "DRUG DELIVERY DEVICE, METHOD OF MANUFACTURE, AND METHOD OF USE"; U.S. Provisional Patent Application No. 62/297,718 entitled "DRUG DELIVERY DEVICE, METHOD OF MANUFACTURE, AND METHOD OF USE"; U.S. Provisional Patent Application No. 62/320,438 entitled "DRUG DELIVERY DEVICE, METHOD OF MANUFACTURE, AND METHOD OF USE"; International Patent Application No. PCT/US2017/017627 entitled "DRUG DELIVERY DEVICE, METHOD OF MANUFACTURE, AND METHOD OF USE"; International Patent Application No. PCT/US2017/026524 entitled "DRUG DELIVERY DEVICE, METHOD OF MANUFACTURE, AND METHOD OF USE"; U.S. Provisional Patent Application No. 62/536,909 entitled DRUG DELIVERY DEVICE WITH CONTAINER ACCESS SYSTEM AND RELATED METHOD OF ASSEMBLY"; AND U.S. Provisional Patent Application No. 62/536,911 entitled "DRUG DELIVERY DEVICE WITH GEAR MODULE AND RELATED METHOD OF ASSEMBLY."

Testing Assembly Disclosure

As a drug is delivered subcutaneously to a patient, the muscle and tissue of the patient at the delivery site are forced to expand, which creates a back pressure that the delivery device overcomes while dispensing of the drug. A testing assembly as described herein advantageously accounts for this pressure for testing the operation of drug delivery devices. The testing assembly can be utilized to simulate the back pressure applied during patient injection and measure an amount of drug delivered by measuring a weight, volume, or other characteristic of the delivered drug, as well as a dispense time for the drug delivery operation by monitoring the delivered drug. The testing assembly can further be adapted to monitor the extension distance of the delivery structure of the drug delivery device, as well as the time to extend and retract the delivery structure.

In further embodiments, the testing assembly can include a force sensor configured to engage and actuate an input device of the drug delivery device to determine a force required to operate the drug delivery device. The dispense time test can be associated with the force sensor setup to time the drug delivery device operation from actuation of the input device to complete delivery of the drug. Moreover, a base plate can be used throughout the testing process for mounting the drug delivery device within the testing assembly. Thereafter, a peel force test can be performed by pulling the drug delivery device off of the base plate. As such, a single drug delivery device can be used in up to seven distinct performance tests, saving time and money and reducing waste.

Figure 3:
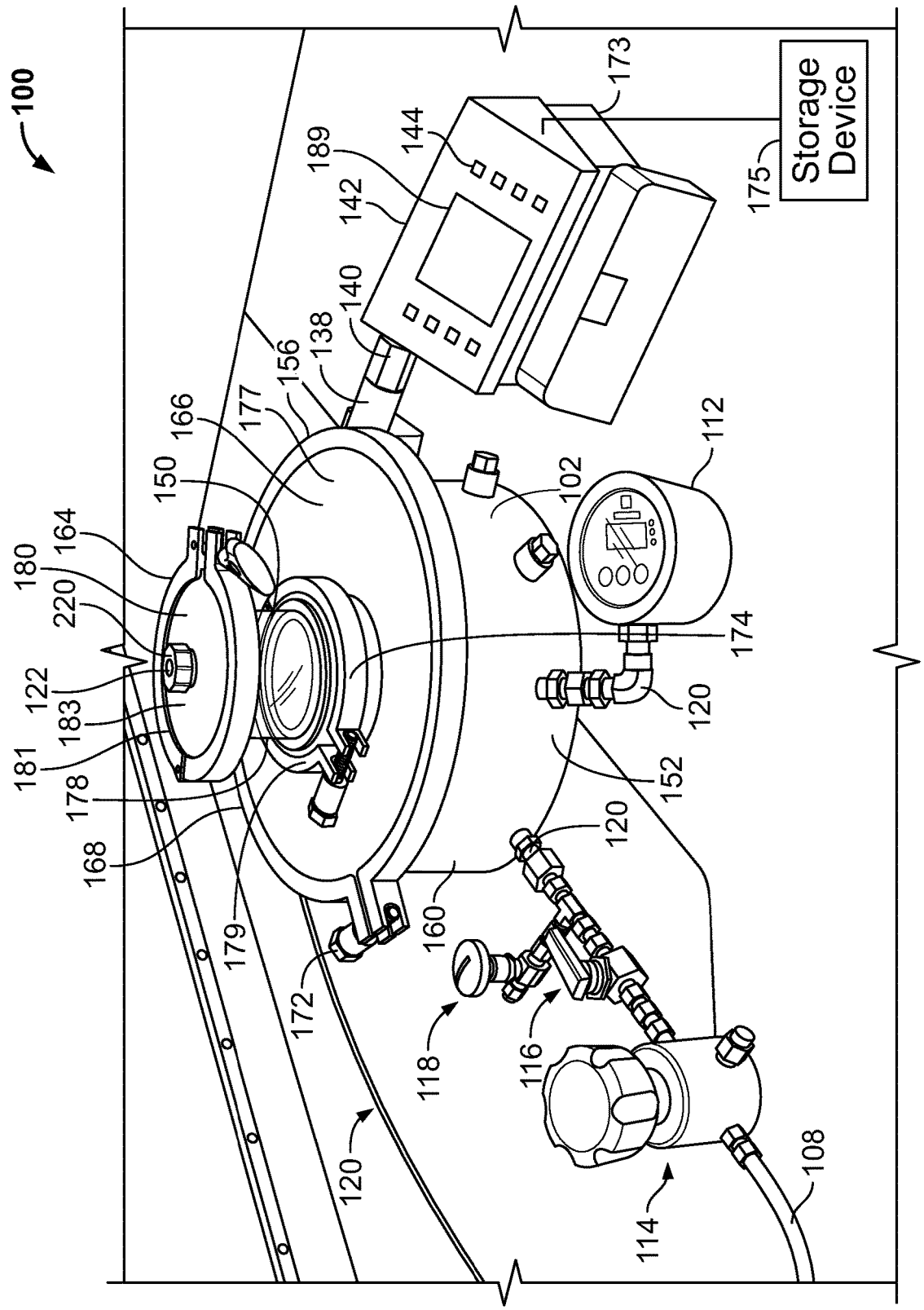
FIG. 3 is a perspective view of a back pressure testing assembly for testing drug delivery devices in accordance with various embodiments.
Figure 4:
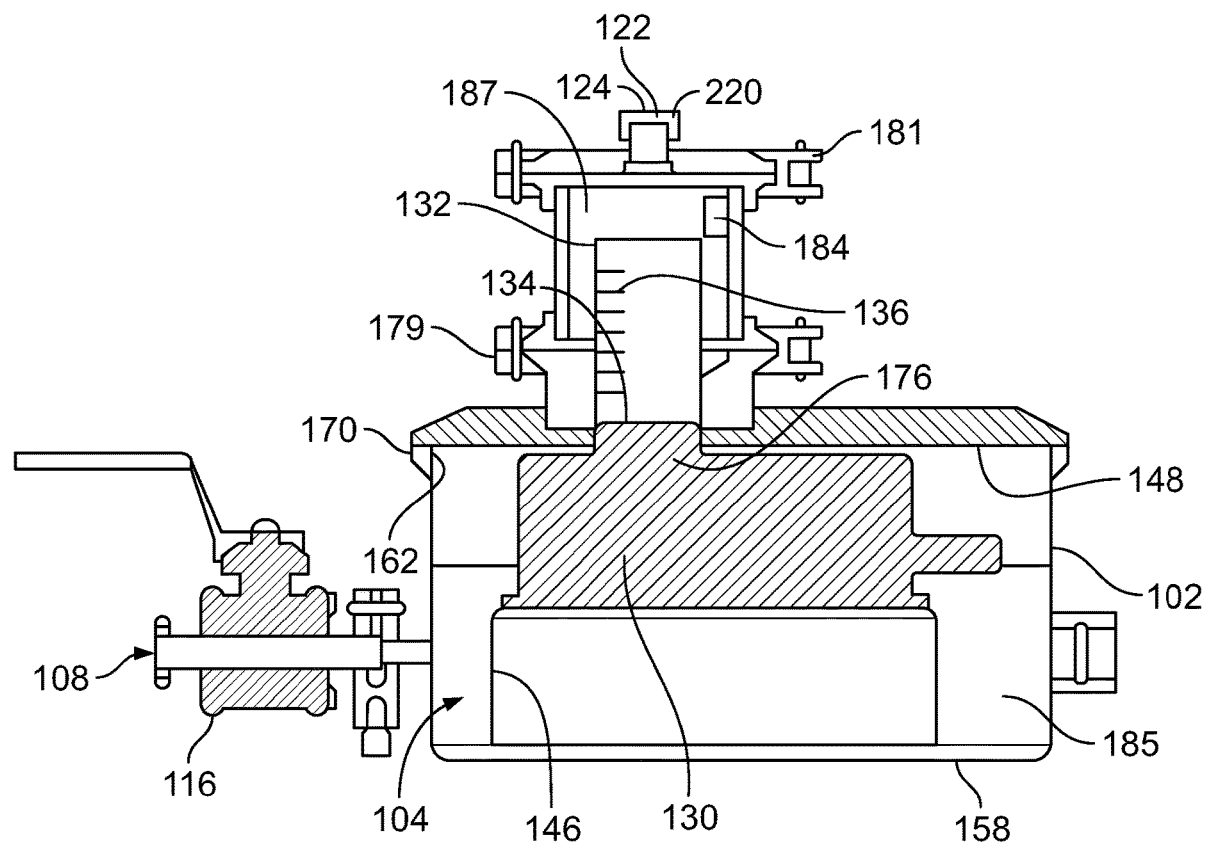
FIG. 4 is a cross-sectional side view of the back pressure testing assembly of FIG. 3 in accordance with various embodiments.

In a first aspect, a back pressure testing assembly 100 for simulating subcutaneous delivery of a drug 32 is shown in FIGS. 3-4. The pressure vessel 102 can include all components for pressurizing, observing, and de-pressurizing the chamber 104 thereof. For example, the testing assembly 100 can include a pressurized gas supply 108 having an on/off valve 116, a pressure gauge 112, a vessel regulator 114, a bleed or pressure relief valve 118, and conduits/pipes 120 connecting the various components to the pressure vessel 102.

So configured, a user can operate the on/off valve 116 to allow the supply 108 to pressurize the pressure vessel 102. The pressure gauge 112 shows the current pressure in the vessel 102 so that a user can operate the on/off valve 116 to shut off the supply 108 when the pressure vessel 102 has a desired pressurization. After tests are completed, a user can then operate the bleed valve 118 to release the pressure. These components, such as the pressure gauge 112 and the valve 116 can be manual, analog devices, or can be electronic and operable by input signals, whether local or remote, as commonly understood.

In one form, the pressure vessel 102 includes a bottom, bowl portion 152 and a lid 166. The bottom portion 152 includes a bottom wall 158 with an annular sidewall 160 extending upwardly from the bottom wall 158 to an upper edge 162 thereof. The lid 166 engages the sidewall upper edge 162 so as to provide a seal therewith. By one approach, the lid 166 is attached to the bottom portion 152 using a clamp 156. As shown, the clamp 156 includes two curved portions 168 that are hingedly connected together. The curved portions 168 have a curvature complementary to the sidewall 160 and lid 166 with a radially inwardly concave configuration so that portions thereof project above the lid 166 and below a rim 170 of the sidewall upper edge 162. The curved portions 168 can then be positioned around the lid 166 and bottom portion 152 and connected together at distal ends thereof opposite the hinge using a fastener 172.

With reference to FIG. 3, the lid 166 includes a plate portion 177 and a stack assembly 164. The stack assembly 164 has a multi-part, tubular construction with a base portion 174, a top member 178, and a cover 180. The base portion 174 secures to the plate portion 177 of the lid 166 by any suitable method, such as welding or the like, while the base portion 174, top member 178, and cover 180 secure together using clamps 179, 181. The clamps 179, 181 can be configured similarly to the clamp 156 described above.

The cover 180 includes a plate portion 183, a cap 220 that defines an injection opening 122 extending therethrough, and a pierceable sterile barrier 124, such as a septum. The septum 124 is removably mounted to the cap 220 so that it extends across and seals the injection opening 122. In the illustrated form, the stack assembly 164 has a cylindrical configuration, but other suitable shapes and sizes can be utilized. So configured, the barrier 124 maintains the pressure within the chamber 104, while also providing a dermal analog through which the delivery structure can extend. The injection opening 122 is disposed so as to be easily accessible for positioning and operation of the drug delivery device 10, 10'.

Turning to FIG. 4, the pressure vessel 102 defines a chamber 104 therein having a lower portion 185 in the bottom 152 and, extending through an opening 176 in the lid 166, an upper portion 187 in the stack assembly 164. The back pressure testing assembly 100 further includes a measuring device 130 and a container or receptacle 132 operably coupled to the measuring device 130 disposed within the chamber 104. As shown, the measuring device 130 is disposed within the lower portion 185 of the chamber 104 and the container 132 is disposed within the upper portion 187. The container 132 is aligned with the injection opening 122 to thereby collect any drug 32 injected into the chamber 104 through the septum 124.

In this configuration, if external power, monitoring, and/or control is desired, the pressure vessel 102 can include a port, conduit, or other opening 138 so that wires or other electrical connections 140 can extend from the measuring device 130, through the port 138, to a power supply and/or one or more secondary devices 142 remote from the pressure vessel 102. The port 138 can be suitably constricted or blocked around the wires so that the pressure vessel 102 maintains a desired pressure therein. Of course, the measuring device 130 can also be battery operated.

In the illustrated form, the measuring device 130 is a scale and the container 132 can be positioned on a weighing surface 134 of the scale 130. The scale 130 can be configured to measure a weight of the drug 32 dispensed by the drug delivery device 10, 10' into the pressure vessel 102 through the septum 124. Using a known density of the drug 32, the volume of drug 32 dispensed can be determined. Moreover, the scale 130 can be utilized to determine a delivery time for the drug 32. For example, software or a user can monitor the time between a first recorded weight measurement of the drug 32 and a final weight change measurement of the drug 32 determined by the scale 130.

One secondary device 142 can be a control unit or circuit 173 for the scale 130 optionally including a display 189 and inputs 144, such as tare, units, on/off, and so forth. Software, operating on the control unit 173, or a user can monitor the weight of the dispensed drug 32 and the time between actuation of the input device 28 of the drug delivery device 10 and complete delivery of the drug 32 based on weight changes measured by the scale 130. With the control unit 173, a user can operate or correct settings on the scale 130 without opening up the pressure vessel 102. The control unit 173 can store data therefrom in any suitable storage device 175 including local and remote storage.

With some configurations, the pressure vessel 102 may have a larger height than desired for positioning the scale 130 near the injection opening 122. Accordingly, if desired and as shown in FIG. 4, the scale 130 can be lifted within the chamber 104, such as by brackets 146, legs, or the like so that the weighing surface 134 is disposed adjacent to a lower surface 148 of the lid 166 and the container 132 is disposed adjacent to the injection opening 122.

As shown, the scale 130 is disposed within the bottom portion 152. Accordingly, with the lid 166 off, a user can position the scale 130 within the bottom portion 152 at a desired location and orientation. For example, the user can install or position the brackets 146 and then mount the scale 130 to the brackets 146. Thereafter, the user can place the container 132 on the scale 130 and secure the lid 166 to the bottom portion 152 using the clamp 156. Alternatively, the scale 130 can be permanently mounted within the bottom portion 152. The user can also release one or both of the clamps 179, 181 of the stack assembly 164, to thereby position, access, and retrieve the container 132.

In another form, the amount of drug 32 dispensed can be visually monitored and measured during use. As such, the pressure vessel 102 can include a transparent or translucent portion 150 providing a view of the drug 32 as it is dispensed. Preferably, the transparent portion 150 is aligned with at least a portion or all of the container 132 so that the user can see the drug 32 as it is collected within the container 132. If the container 132 has volume indicators 136, visually monitoring the container 132 can also provide an indication or confirmation of a volume of drug 32 dispensed.

In the illustrated form, the stack assembly 164, and specifically the upper member 178 thereof, includes the transparent portion 150. For example, the upper member 178 can be made of a transparent or translucent material or include a transparent or translucent portion. The material of the upper member 178 can be a suitable glass or plastic material. Further, the upper portion 187 of the chamber 104 is preferably sized to receive the container 132 therein so that the container 132, and the dispensed drug 32, is easily viewable by a user.

Moreover, as shown in FIG. 4, the stack assembly 164 is configured so that the injection opening 122 is visible through the transparent portion 150. As such, the extension of the delivery structure can be visually monitored during delivery of the drug 32. This provides yet another operation test for the drug delivery device 10, 10'. The delivery structure should extend a distance to pierce the skin of a patient and reach a suitable subcutaneous position.

Moreover, a camera device 184 (see FIG. 4) can be mounted outside of or within the pressure vessel 102 adjacent to the injection opening 122 with any of the above-described embodiments, such as to the cover 180, upper member 178, lid 166, sidewall 160, and so forth. The camera device 184 can capture images or video of the injection and the extension of the delivery structure. If desired, the camera device 184 can be oriented to capture images and/or video of the extension and retraction of the delivery structure so that the testing assembly 100 thereby performs additional tests regarding measuring the extension amount, as well as extension and retraction times. The camera device 184 can be operated by the control unit 173 and the data captured thereby can be stored in the storage device 175. Of course, the control unit 173 and storage device 175 can be separate from the ones described above with respect to the scale 130.

As described, the back pressure testing assembly 100 is suitable to test the operation of any suitable drug delivery devices, such as on-body injectors 10 and autoinjectors 10'. With the above configuration, a user can optionally set up the scale 130 within the pressure chamber 104, attach the lid 166 using the clamp 156, position the container 132 on the scale 130, and attach the components 174, 178 of the stack assembly 164 together and to the plate portion 177 of the lid 166. Using the clamps 179, 181 of the stack assembly 164, a user can then easily access the container 132 to remove the drug 32 after a completed test without completely disassembling the pressure vessel 102.

Once assembled, the user can operate the on/off valve 116 to allow the supply 108 to pressurize the pressure vessel 102. The pressure vessel 102 is configured to be pressurized to a range of pressures corresponding to pressures experienced during operation of the drug delivery device 10, 10' on a patient. For example, the pressure vessel 102 be pressurized to a range of 0 psi to about 20 psi, and more particularly between about 2 psi and about 15 psi, and more particularly between about 5 psi and about 10 psi.

Figure 5:
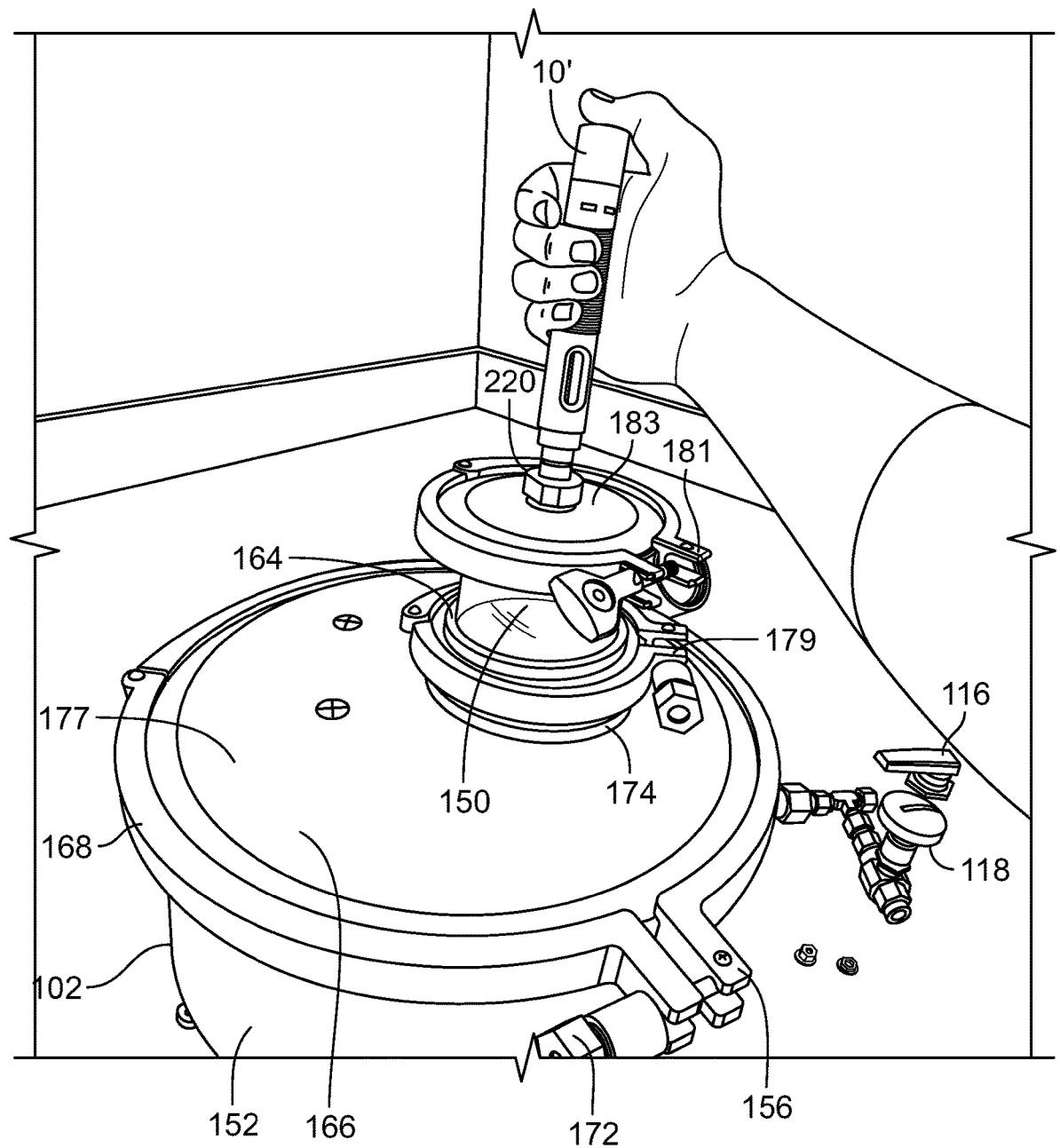
FIG. 5 is a perspective view of the back pressure testing assembly of FIG. 3 showing the testing of an autoinjector drug delivery device in accordance with various embodiments.

After pressurization, the drug delivery device 10, 10' can be placed or mounted adjacent to the opening 122 and operated. More specifically, the insertion mechanism 12 of the device 10, 10' can then insert a needle, trocar 21 and cannula 23, or other delivery structure into the pressure chamber 104 to dispense the drug 32 into the container 132 to be measured by the scale. One example with an autoinjector drug delivery device 10' is shown in FIG. 5.

It will be understood that numerous alternative embodiments could be implemented. For example, the injection opening 122 can be provided in any desired location of and/or orientation with respect to the pressure vessel 102. Further, if desired, the pressure vessel 102 can be provided without the stack assembly 164 and the injection opening 122 can be provided in the plate portion 177. Further, the plate portion 177 or an area thereof can be transparent or translucent to provide a view of the drug delivery and the amount thereof. Other measurement devices can also be utilized, such as a hanging scale having the container 132 depend therefrom, a float sensor configured to be disposed within the container 132, a flow rate sensor configured to measure the flow of the drug 32 as it is dispensed, an optical sensor, and so forth. As such, the various measurement devices can measure the dose of the drug by weight, volume, and flow rate along with dispense time.

Figure 6:
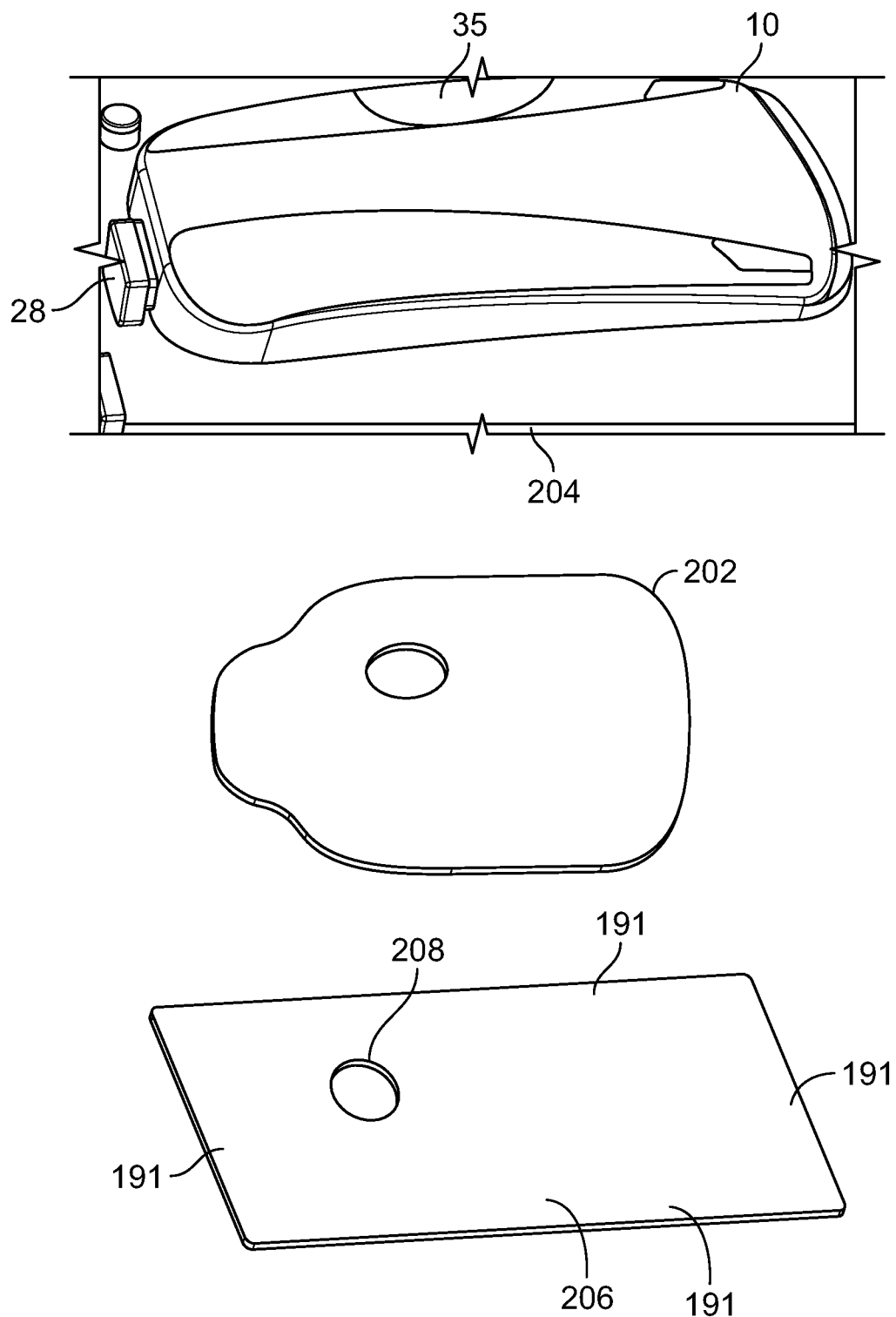
FIG. 6 is an exploded view of a drug delivery device, adhesive patch, and base plate in accordance with various embodiments.
Figure 12:
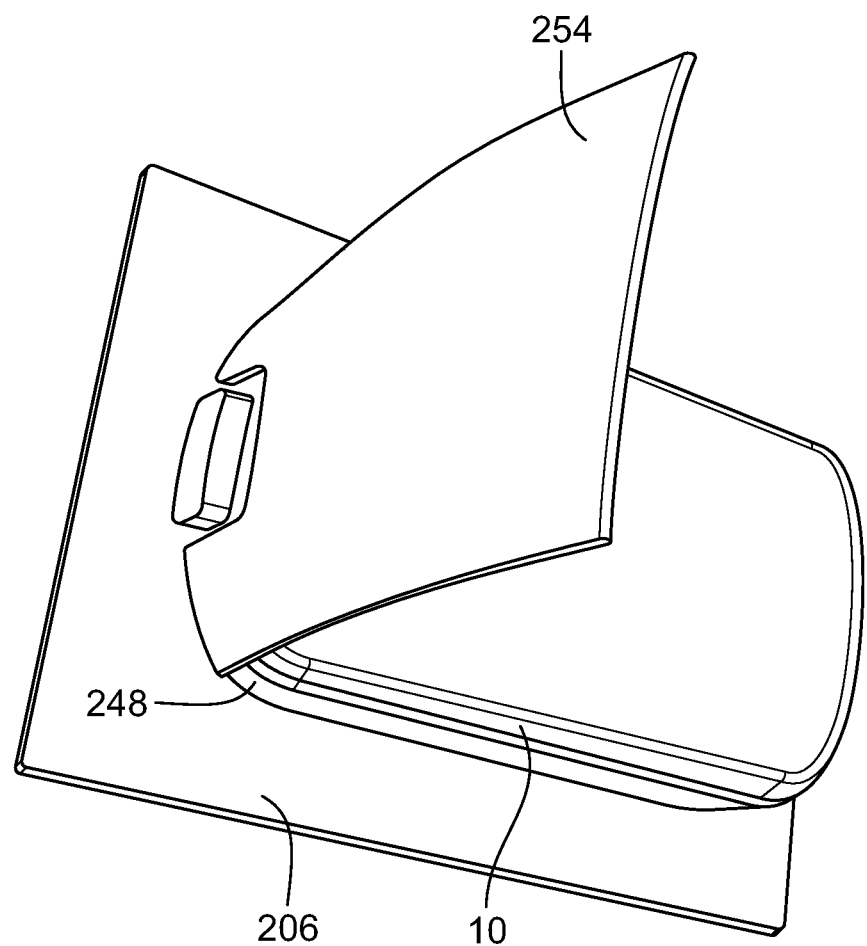
FIG. 12 is a top perspective view of the drug delivery device mounted to a base plate with a peel force member attached thereto in accordance with various embodiments.

As shown in FIG. 6, the drug delivery device 10 is a wearable drug delivery device having an adhesive or an adhesive patch 202 applied to a bottom surface 204 thereof so that a patient can adhere the device 10 to a desired portion of skin. For testing purposes, the adhesive/adhesive patch 202 can be utilized to adhere the device 10 to a base plate 206 (see FIG. 12). The base plate 206 includes an opening 208 extending therethrough that aligns with the delivery mechanism 12 of the device 10, so that the delivery structure can pass through the opening 208. As shown, the footprint of the base plate 206 is larger than the device 10 so that edge portions 191 thereof project outwardly from the device 10.

Figure 7:
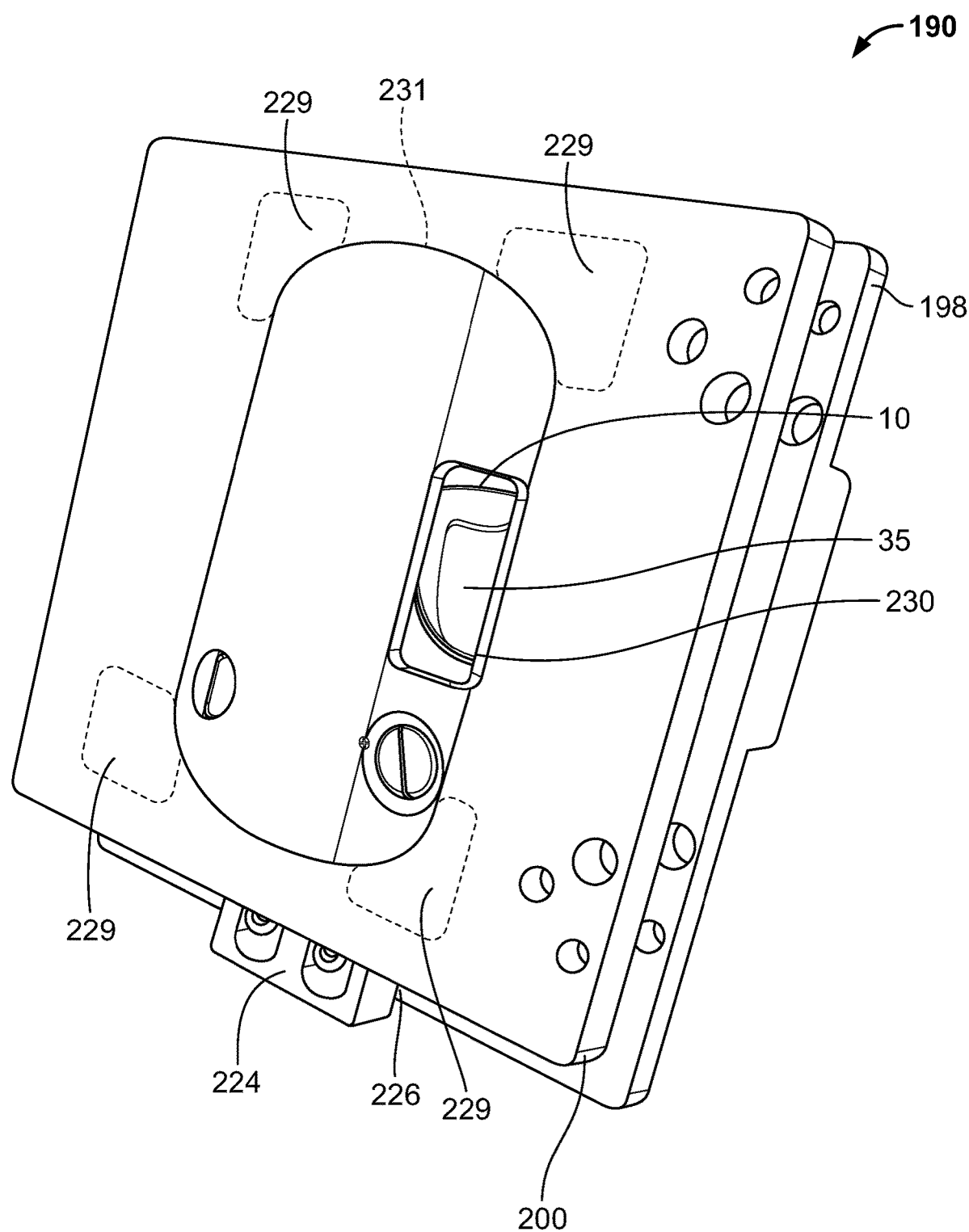
FIG. 7 is a top perspective view of a device housing for mounting a drug delivery device to the back pressure testing assembly of FIG. 3 showing a drug delivery device received therein in accordance with various embodiments.
Figure 8:
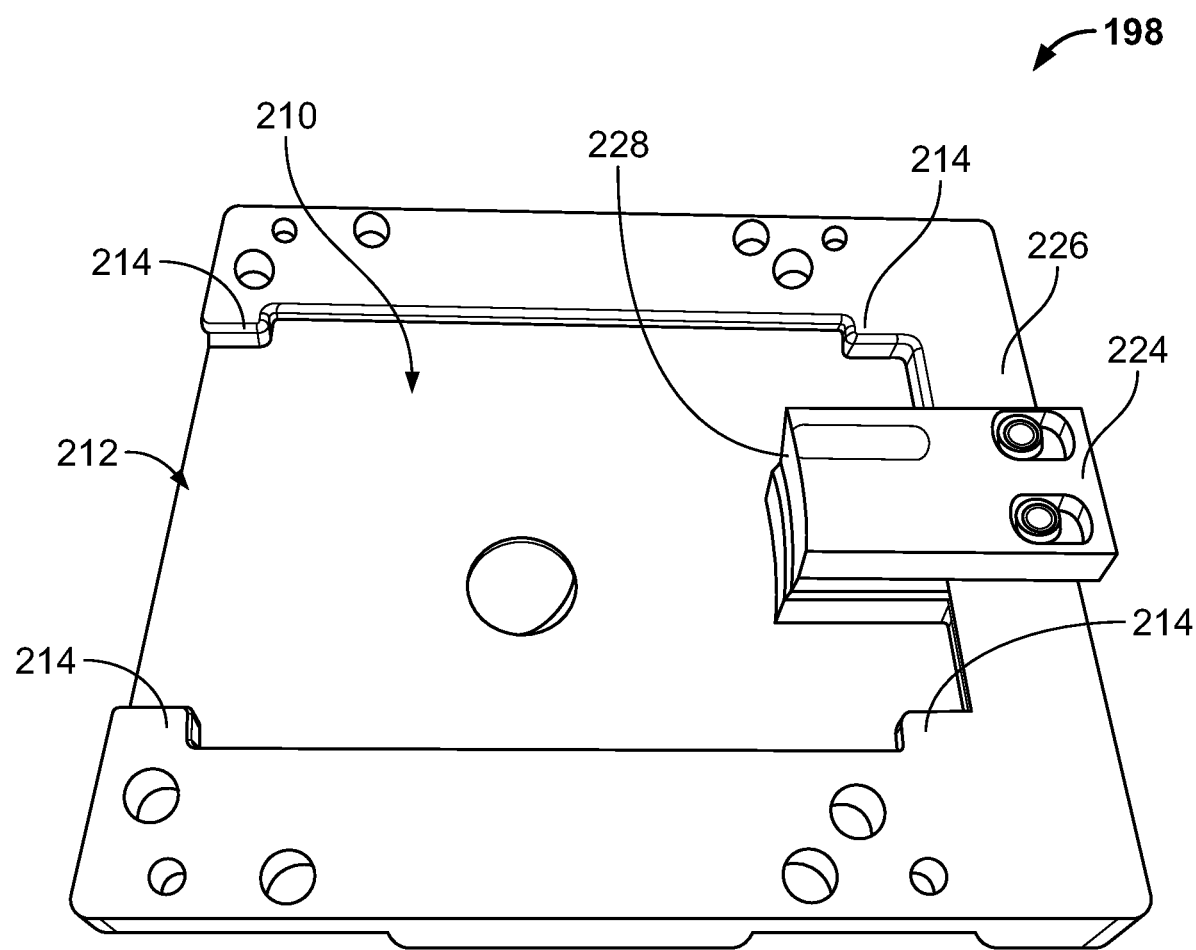
FIG. 8 is a top perspective view of a base portion of the device housing of FIG. 7 with a base plate for a drug delivery device received therein in accordance with various embodiments.
Figure 9:
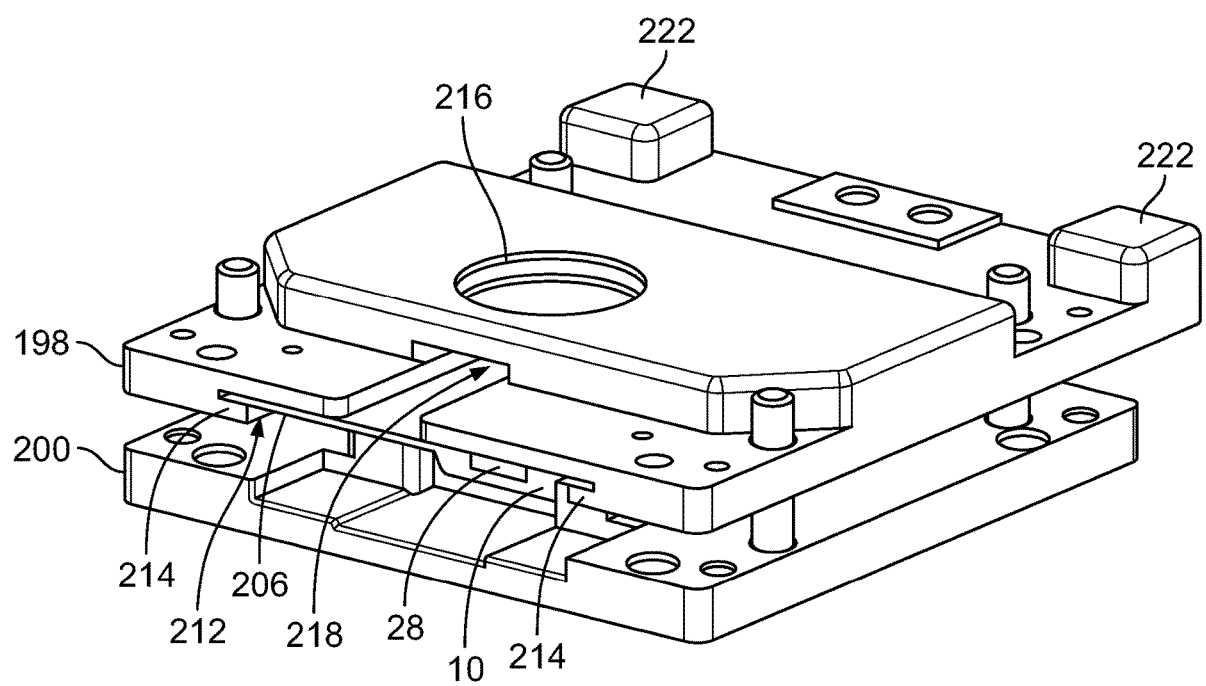
FIG. 9 is a bottom perspective view of the device housing of FIG. 7 in accordance with various embodiments.

As shown in FIGS. 7-9, the device 10, 10' can be secured to the pressure vessel 102 using a device housing 190 that includes a base member 198 and a cover member 200 that capture the drug delivery device 10 and the base plate 206 therebetween.

With reference to FIG. 7, the cover member 200 of the device housing 190 attaches to the base member 198 to trap the device 10 and base plate 206 therebetween. The cover member 200 can include downwardly depending walls 229 and/or a recess configured to extend adjacent to and engage sidewalls 231 of the device 10 to thereby hold the device 10 in place during testing. The base and cover members 198, 200 can secured together by any suitable mechanism, such as fasteners, as shown, a hinged connection, snap fit, and so forth.

If desired, the cover member 200 can include an opening 230 extending therethrough that is configured to align with the window 35 of the drug dispensing device 10 so that a user can determine an amount of drug 32 left within the device 10.

Turning now to FIG. 8, the base member 198 includes an upwardly facing recess 210 with an outwardly facing opening 212. Overhang portions 214 extend over the recess 210, such as at the rear corners and along a front edge thereof as shown. The base plate 206, with the device 10 adhered thereto, can be slid into the recess 210 through the outwardly facing opening 212 such that the overhang portions 214 restrict the base plate 206 from being lifted upward.

The base member 198 can include a stop member 224 that ensures proper alignment of the device 10 on the base member 198, such as for repeated tests of the same type of device design. The stop member 224 extends out over the recess 210 and abuts the device 10 as the device 10 is inserted onto the base member 198. As such, the stop member 224 thereby ensures that the device 10 is aligned properly on the base member.

In the illustrated form, the stop member 224 extends forwardly from a rear portion 226 of the base member 198 so that the device 10 is installed at the correct depth of the base member 198. Further, the stop member 224 includes an engagement surface 228 that is complementary to the device 10, e.g., a complementary curved configuration, so that the stop member 224 can also laterally align the device 10 within the base member 198. If desired although not shown, the base member 198 can include stop members on sides thereof in addition to the rear stop member 224. Moreover, although the stop member 224 is shown attached to the base member 198 using fasteners, other suitable securing mechanisms can also be utilized or the base member 198 and stop member 224 can have a single-piece construction.

As shown in FIG. 9, the base member 198 further includes a through-opening 216 and a recessed channel 218. The through-opening 216 aligns with the opening 208 of the base plate 206 and the delivery mechanism of the device 10 when the base plate 206 and device 10 are slid into the recess 210. The recessed channel 218 extends between the opening 216 and the front edge of the base member 198. The channel 218 is preferably sized so that, as shown in FIG. 10, a full extension of the delivery structure can be viewed therethrough.

The base member 198 is configured to couple to the pressure vessel 102 (see FIG. 10), and specifically the cap 220 thereof, to thereby ensure proper alignment between the septum 124 and the drug delivery device 10. The through-opening 216 has a shape complementary to the cap 220 so that the cap 220 can be received therein when the base member 198 is mounted to the pressure vessel 102. Preferably, the through-opening 216 is sized so that the cap 220 abuts the base plate 206 through the base member 198 so that the septum 124 is disposed closely adjacent to the delivery mechanism of the drug delivery device 10. If desired, the thickness of the base member 198 can be increased around the through-opening 216 to generally match the height of the cap 220. Further, the base member 198 can include foot projections 222 on an opposite side of the base member 198 from the through-opening 216 to provide stability for the device housing 190.

Figure 10:
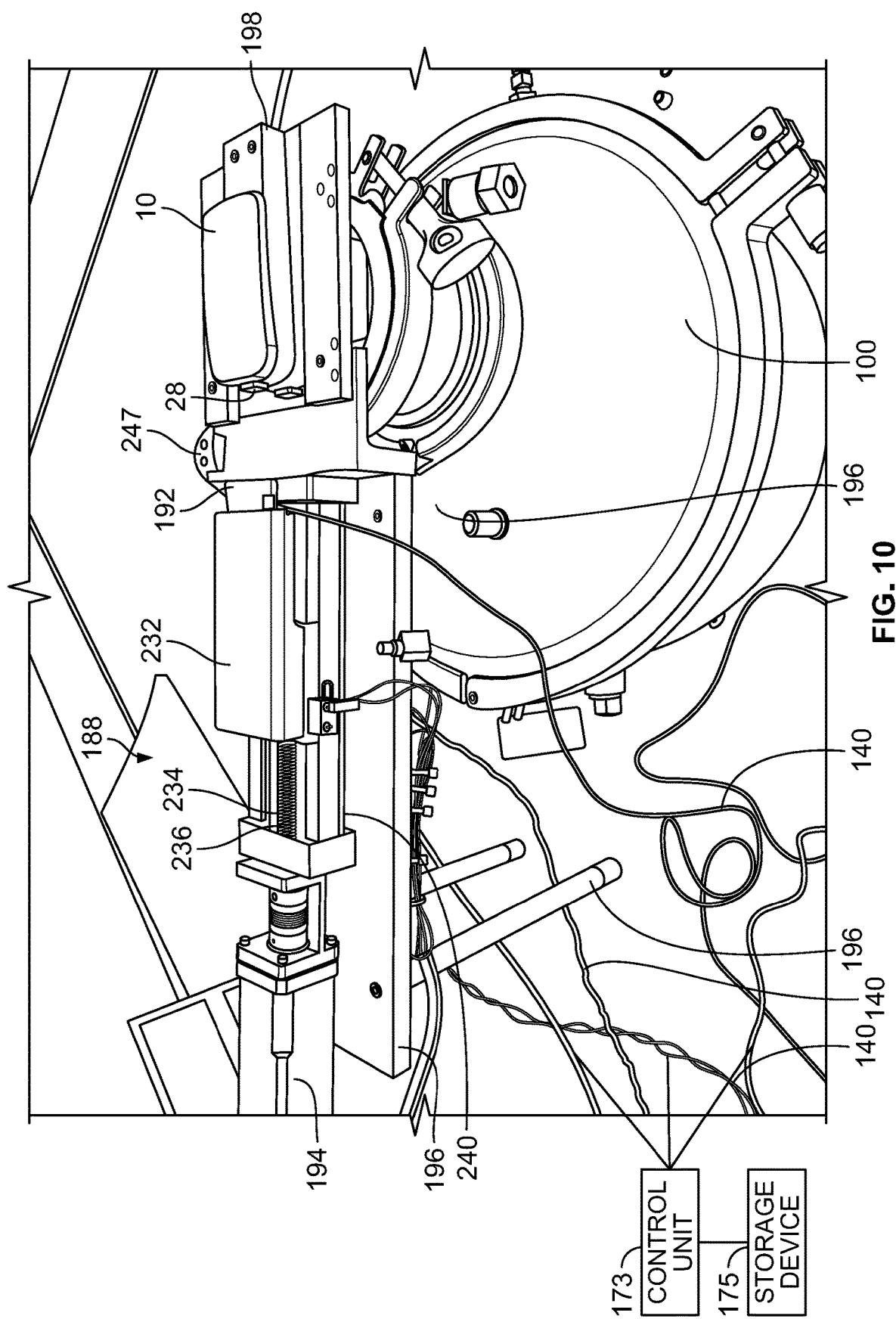
FIG. 10 is a perspective view of a testing assembly for drug delivery devices including the back pressure testing assembly of FIG. 3, the device housing of FIG. 7, and an actuation force assembly in accordance with various embodiments.

As shown in FIG. 10, the back pressure testing assembly 100 and the device housing 190 can be incorporated with an actuation force test assembly 188 that advantageously tests the force required to actuate the input device 28 of the drug delivery device 10. The actuation force test assembly 188 utilizes the device housing 190 to hold the drug delivery device 10 during testing, and includes a force sensor 192, a drive mechanism 194, a drive shaft 234, a mount 232, and support structure 196 therefor.

The force sensor 192 is secured to the mount 232 and the drive mechanism 194 is operably coupled to the mount 232 so that operation of the drive mechanism 194 shifts the force sensor 192 into engagement with the activation button 28 of the drug delivery device 10. The drive mechanism 194 can be any suitable device, such as a motor, actuator, and so forth. If desired, operation of the drive 194 can be controlled by the control unit 173.

The force sensor 192 is mounted on a forward portion 246 of the mount 232 and projects forwardly thereof. As such, as the mount 232 is driven along the drive shaft 234, the force sensor 192 provides the leading surface for the mount 232.

As shown, the actuation force test assembly 188 is coupled or mounted adjacent to the device housing 190 so that the mount 232 on the drive shaft 234 is aligned with the drug delivery device 10 within the device housing 190 and, more specifically, the force sensor 192 is aligned with the activation button 28 of the drug delivery device 10. So configured, as the drive 194 advances the mount 232 along the drive shaft 234, the force sensor 192 is driven into engagement with the activation button 28. Thereafter, the force sensor 192 can measure the force required to press or actuate the activation button 28.

By a further approach, the actuation force test assembly 188 can include a timer sensor or switch device 247 mounted to the track 240 at a position coinciding with the force sensor 192 actuating the input device 28 of the drug delivery device 10. As such, the timer is started at the same time that the force sensor 192 operates the drug delivery device 10. The timer sensor 247 can be coupled to and controlled by the control unit 173. Moreover, the dispense time can be stored by the control unit 173 on the storage device 175. The timer sensor 247 can be configured to activate a timer to, in combination with the scale 130, measure operation time for the drug delivery device 10.

The term control unit as utilized herein refers broadly to any microcontroller, computer, or processor-based device with processor, memory, and programmable input/output peripherals, which is generally designed to govern the operation of other components and devices. It is further understood to include common accompanying accessory devices, including memory, transceivers for communication with other components and devices, etc. These architectural options are well known and understood in the art and require no further description here. The control unit 173 may be configured (for example, by using corresponding programming stored in a memory as will be well understood by those skilled in the art) to carry out one or more of the steps, actions, and/or functions described herein. Moreover, although the control unit 173 is referenced herein as a single device, the components described herein can be controlled by separate control units, or by any desired combination of control units.

Figure 11:
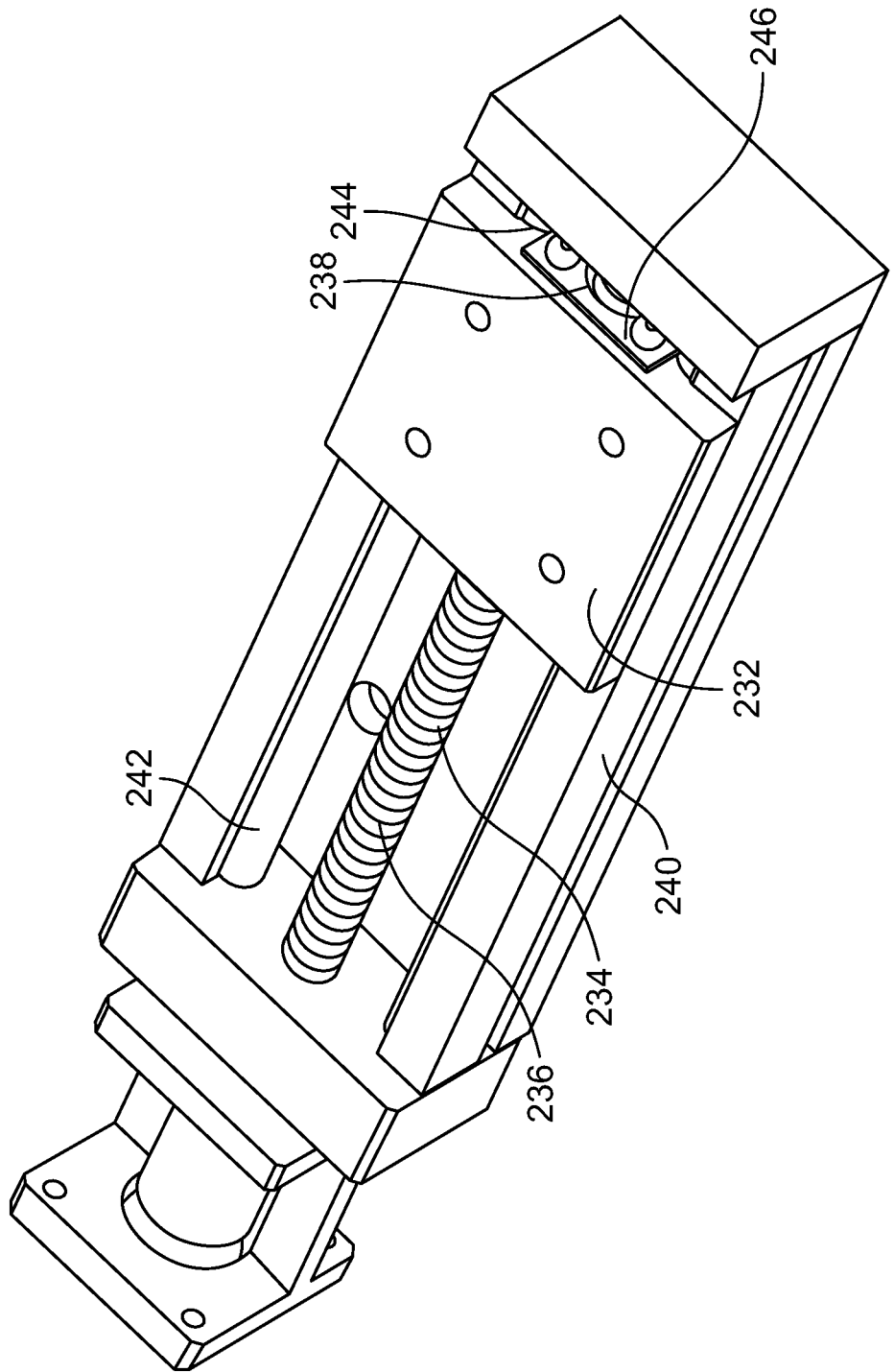
FIG. 11 is a top perspective view of a portion of the actuation force assembly of FIG. 10 in accordance with various embodiments.

With reference to FIG. 11, the mount 232 includes an internally threaded opening 238 and the drive shaft 234 has a thread 236 extending therearound so that the mount 232 threadingly couples to the drive shaft 234. As such, when the drive mechanism 194 rotates the drive shaft 234, the mount 232 is driven axially therealong.

In order to hold the mount 232 in a steady horizontal orientation, the force test assembly 188 can include a track 240 along which the mount 232 is driven that includes a guide member 242 disposed laterally adjacent to the drive shaft 234 and the mount 232 includes a corresponding opening or recess 244 that slides along the guide member 242 as the mount 232 is driven along the drive shaft 234. The engagement between the guide member 242 and the recess 244 restricts rotation of the mount 232 so that the mount 232 maintains a level horizontal orientation while it is driven along the drive shaft 234. The track 240 includes two laterally disposed cylindrical or partially-cylindrical guide members 242 and the mount 232 includes longitudinal recesses 244 slidingly receiving the guide member 242.

This configuration effectively and advantageously uses the same drug delivery device 10 to test button actuation force, drug delivery time, drug delivery amount, and delivery structure extension, which can save time and money and reduce waste.

As discussed previously, the drug delivery device 10 is attached to the base plate 206 using the adhesive or adhesive patch 202, which simulates on-body mounting of the drug delivery device 10. After use by a patient, the device 10 must be removed from the patient's skin. Thus, the system described herein can further be configured to facilitate a test for determining what force is required to remove the device 10 from the base plate 206, thereby simulating removal of the device 10 from a patient's skin.

Figure 13:
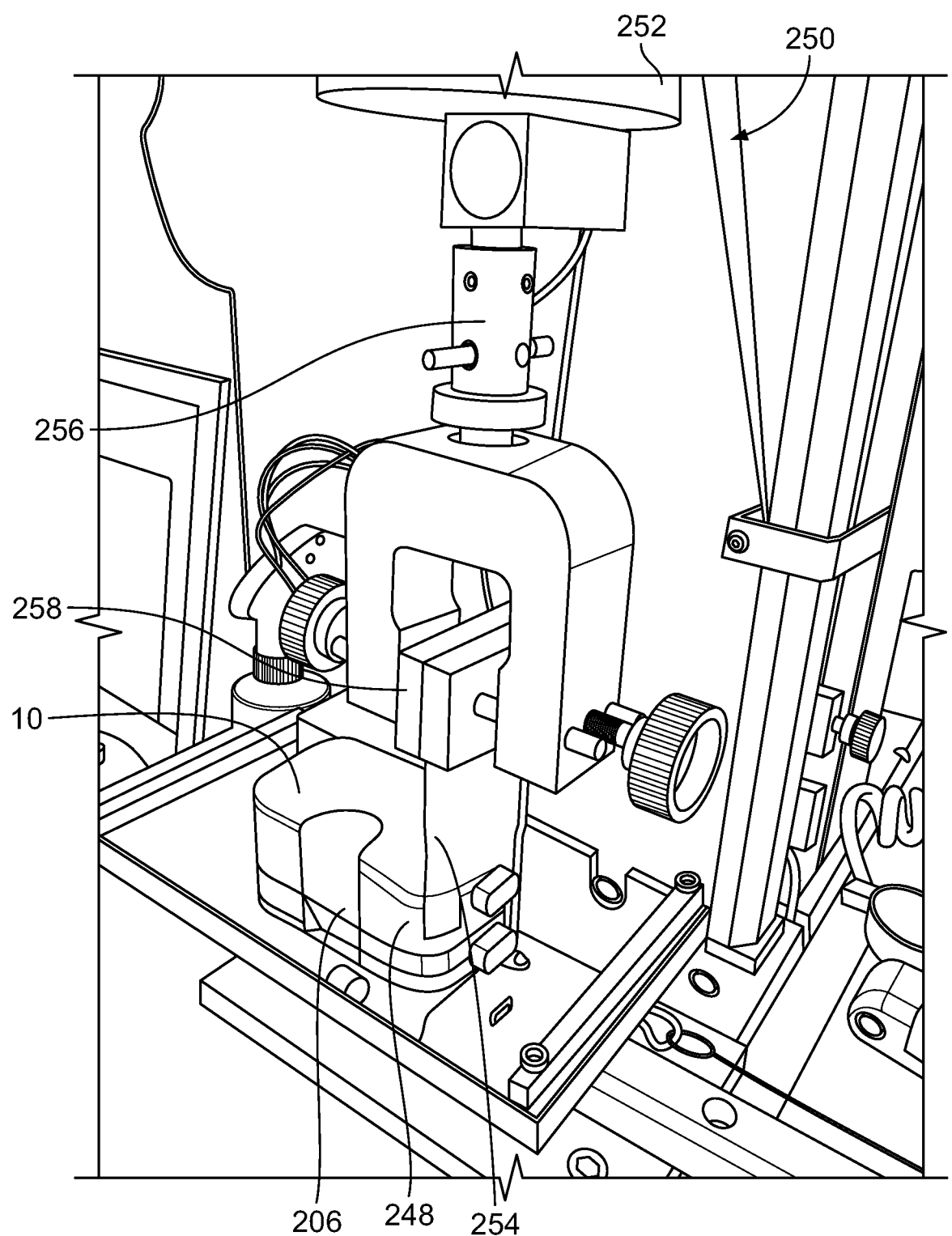
FIG. 13 is a perspective view of a peel force assembly with a tension force machine coupled to the drug delivery device through the peel force member of FIG. 12 in accordance with various embodiments.

During removal, a user typically grips the device 10 at either end 248 thereof and pulls the end of the device 10 away from the skin. Accordingly, in the peel test setup 250 shown in FIGS. 12 and 13, a user secures the base plate 206 within a tension machine 252 and couples a pull member 254 to the end 248 of the device 10 and to the machine 252. Thereafter, the machine 252 operates to pull the device 10 off of the base plate 206 by pulling on the member 254. The tension machine 252 is monitored to determine a max force required during the removal procedure. In the illustrated form, the tension machine 252 is an Instron™ machine and an arm 256 of the Instron™ machine 252 couples to the pull member 254 using a clamp 258. The pull member 254 can couple to the device 10 by any suitable method, such as adhesive as shown, a hook, a hook and loop fastener, or the like.

Accordingly, utilizing the testing setups and configurations provided herein, one device can be used to perform a plurality of tests on a single drug delivery device 10 rather than requiring a completely different test device for each separate test.

It is noted that the construction and arrangement of the drug delivery device and its various components and assemblies as shown in the various exemplary embodiments is illustrative only. Although only a few embodiments of the subject matter at issue have been described in detail in the present disclosure, those skilled in the art who review the present disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter disclosed herein. For example, elements shown as integrally formed may be constructed of multiple parts or elements, and vice versa. Also, the position of elements may be reversed or otherwise varied, and the nature or number of discrete elements or positions may be altered or varied. Accordingly, all such modifications are intended to be included within the scope of the present disclosure as defined in the appended claims. Furthermore, the order or sequence of any process or method steps may be varied or re-sequenced according to alternative embodiments. Other substitutions, modifications, changes and omissions may be made in the design, operating conditions and arrangement of the various exemplary embodiments without departing from the scope of the present disclosure. The detailed description is to be construed as exemplary only and does not describe every possible embodiment of the invention because describing every possible embodiment would be impractical, if not impossible. Numerous alternative embodiments could be implemented, using either current technology or technology developed after the filing date of this patent that would still fall within the scope of the claims defining the invention.

It should be understood that the legal scope of the invention is defined by the words of the claims set forth at the end of this patent. The appended claims should be construed broadly to include other variants and embodiments of same, which may be made by those skilled in the art without departing from the scope and range of equivalents of the device, drive damper mechanisms, systems, methods, and their elements.

Drug Boilerplate

The above description describes various systems and methods for use with a drug delivery device 10. It should be clear that the testing assemblies, drug delivery device, or methods can further comprise use of a medicament listed below with the caveat that the following list should neither be considered to be all inclusive nor limiting. The medicament will be contained in a reservoir. In some instances, the reservoir is a primary container that is either filled or pre-filled for treatment with the medicament. The primary container can be a cartridge or a pre-filled syringe.

For example, the drug delivery device or more specifically the reservoir of the device may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the drug delivery device may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications, each of which is herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publication Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; U.S. Publication Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publication Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgastrim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RAN KL specific antibodies, peptibodies and the like), including fully humanized and human OPGL specific antibodies, particularly fully humanized monoclonal antibodies, including but not limited to the antibodies described in PCT Publication No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of sequence identification number: 2 as set forth therein in FIG. 2 and/or the heavy chain of sequence identification number: 4, as set forth therein in FIG. 4, each of which is individually and specifically incorporated by reference herein in its entirety fully as disclosed in the foregoing publication;

Myostatin binding proteins, peptibodies, and related proteins, and the like, including myostatin specific peptibodies, particularly those described in U.S. Publication No. 2004/0181033 and PCT Publication No. WO 2004/058988, which are incorporated by reference herein in their entirety particularly in parts pertinent to myostatin specific peptibodies, including but not limited to peptibodies of the mTN8-19 family, including those of sequence identification numbers: 305-351, including TN8-19-1 through TN8-19-40, TN8-19 con1 and TN8-19 con2; peptibodies of the mL2 family of sequence identification numbers: 357-383; the mL15 family of sequence identification numbers: 384-409; the mL17 family of sequence identification numbers: 410-438; the mL20 family of sequence identification numbers: 439-446; the mL21 family of sequence identification numbers: 447-452; the mL24 family of sequence identification numbers: 453-454; and those of sequence identification numbers: 615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publication No. WO 2005/047331 or PCT Application No. PCT/US2004/37242 and in U.S. Publication No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publication No. 2004/097712, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned publication;

Ang2 specific antibodies, peptibodies, and related proteins, and the like, including but not limited to those described in PCT Publication No. WO 03/057134 and U.S. Publication No. 2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2xL1(N); 2xL1(N) WT; Con4 (N), Con4 (N) 1K WT, 2xCon4 (N) 1K; L1C; L1C 1K; 2xL1C; Con4C; Con4C 1K; 2xCon4C 1K; Con4-L1 (N); Con4-L1C; TN-12-9 (N); C17 (N); TN8-8(N); TN8-14 (N); Con 1 (N), also including anti-Ang 2 antibodies and formulations such as those described in PCT Publication No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; AblA1; AblF; AblK, AblP; and AblP, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in U.S. Publication No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publication No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing publication;

Also among non-limiting examples of anti-IGF-1R antibodies for use in the methods and compositions of the present invention are each and all of those described in:

(i) U.S. Publication No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publication No. WO 06/138729 (published Dec. 28, 2006) and WO 05/016970 (published Feb. 24, 2005), and Lu et al. (2004), J. Biol. Chem. 279:2856-2865, including but not limited to antibodies 2F8, A12, and IMC-A12 as described therein;

(iii) PCT Publication No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

(iv) U.S. Publication No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

(v) U.S. Publication Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al. (2003), Cancer Res. 63:5073-5083, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), U.S. Publication Nos. 2005/0244408 (published Nov. 30, 2005) and 2004/0086503 (published May 6, 2004), and Cohen, et al. (2005), Clinical Cancer Res. 11:2063-2073, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) U.S. Publication Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (y4), deposited at the ATCC under number PTA-5214, and a light chain encoded by a polynucleotide in plasmid 15H12/19D12 LCF (K), deposited at the ATCC under number PTA-5220, as described therein; and (viii) U.S. Publication No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publication No. 2008/0166352 and PCT Publication No. WO 07/011941, which are incorporated herein by reference in their entireties as to such antibodies and related proteins, including but not limited to antibodies designated therein as follow: 16H (having light chain variable and heavy chain variable sequences sequence identification number: 1 and sequence identification number: 7 respectively therein); 5D (having light chain variable and heavy chain variable sequences, sequence identification number: 2 and sequence identification number: 9 respectively therein); 2H (having light chain variable and heavy chain variable sequences, sequence identification number: 3 and sequence identification number: 10 respectively therein); 43H (having light chain variable and heavy chain variable sequences sequence identification number: 6 and sequence identification number: 14 respectively therein); 41H (having light chain variable and heavy chain variable sequences sequence identification number: 5 and sequence identification number: 13 respectively therein); and 15H (having light chain variable and heavy chain variable sequences, sequence identification number: 4 and sequence identification number: 12 respectively therein), each of which is individually and specifically incorporated by reference herein in its entirety fully as disclosed in the foregoing publication;

IL-15 specific antibodies, peptibodies, and related proteins, and the like, such as, in particular, humanized monoclonal antibodies, particularly antibodies such as those disclosed in U.S. Publication Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 146B7;

IFN gamma specific antibodies, peptibodies, and related proteins and the like, especially human IFN gamma specific antibodies, particularly fully human anti-IFN gamma antibodies, such as, for instance, those described in U.S. Publication No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing publication and in Thakur et al. (1999), Mol. Immunol. 36:1107-1115. In addition, description of the properties of these antibodies provided in the foregoing publication is also incorporated by reference herein in its entirety. Specific antibodies include those having the heavy chain of sequence identification number: 17 and the light chain of sequence identification number: 18; those having the heavy chain variable region of sequence identification number: 6 and the light chain variable region of sequence identification number: 8; those having the heavy chain of sequence identification number: 19 and the light chain of sequence identification number: 20; those having the heavy chain variable region of sequence identification number: 10 and the light chain variable region of sequence identification number: 12; those having the heavy chain of sequence identification number: 32 and the light chain of sequence identification number: 20; those having the heavy chain variable region of sequence identification number: 30 and the light chain variable region of sequence identification number: 12; those having the heavy chain sequence of sequence identification number: 21 and the light chain sequence of sequence identification number: 22; those having the heavy chain variable region of sequence identification number: 14 and the light chain variable region of sequence identification number: 16; those having the heavy chain of sequence identification number: 21 and the light chain of sequence identification number: 33; and those having the heavy chain variable region of sequence identification number: 14 and the light chain variable region of sequence identification number: 31, as disclosed in the foregoing publication. A specific antibody contemplated is antibody 1119 as disclosed in the foregoing U.S. publication and having a complete heavy chain of sequence identification number: 17 as disclosed therein and having a complete light chain of sequence identification number: 18 as disclosed therein;

TALL-1 specific antibodies, peptibodies, and the related proteins, and the like, and other TALL specific binding proteins, such as those described in U.S. Publication Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in U.S. Publication No. 2005/0118643 and PCT Publication No. WO 2005/017107, huL2G7 described in U.S. Pat. No. 7,220,410 and OA-5d5 described in U.S. Pat. Nos. 5,686,292 and 6,468,529 and in PCT Publication No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2;

Activin A specific antibodies, peptibodies, related proteins, and the like, including but not limited to those described in U.S. Publication No. 2009/0234106, which is herein incorporated by reference in its entirety, particularly in parts pertinent to proteins that bind Activin A;

TGF-beta specific antibodies, peptibodies, related proteins, and the like, including but not limited to those described in U.S. Pat. No. 6,803,453 and U.S. Publication No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publication No. WO 2006/081171, which is herein incorporated by reference in its entirety, particularly in parts pertinent to proteins that bind amyloid-beta proteins. One antibody contemplated is an antibody having a heavy chain variable region comprising sequence identification number: 8 and a light chain variable region having sequence identification number: 6 as disclosed in the foregoing publication;

c-Kit specific antibodies, peptibodies, related proteins, and the like, including but not limited to those described in U.S. Publication No. 2007/0253951, which is incorporated herein by reference in its entirety, particularly in parts pertinent to proteins that bind c-Kit and/or other stem cell factor receptors;

OX40L specific antibodies, peptibodies, related proteins, and the like, including but not limited to those described in U.S. Publication No. 2006/0002929, which is incorporated herein by reference in its entirety, particularly in parts pertinent to proteins that bind OX40L and/or other ligands of the 0X40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4ß7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-05 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgastrim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti-α4integrin mAb); Valortim® (MDX-1303, anti-*B. anthracis* protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Ra mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxinl mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/1L23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFß mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab), as well as molecules, variants, analogs or derivatives thereof as disclosed in the following patents or patent applications, each of which is herein incorporated by reference in its entirety for all purposes: U.S. Pat. No. 8,030,547, U.S. Publication No. 2013/0064825, WO2008/057457, WO2008/057458, WO2008/057459, WO2008/063382, WO2008/133647, WO2009/100297, WO2009/100318, WO2011/037791, WO2011/053759, WO2011/053783, WO2008/125623, WO2011/072263, WO2009/055783, WO2012/0544438, WO2010/029513, WO2011/111007, WO2010/077854, WO2012/088313, WO2012/101251, WO2012/101252, WO2012/101253, WO2012/109530, and WO2001/031007.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223,593 and 7,537,924); OncoVEXGALV/CD (U.S. Pat. No. 7,981,669); OrienX010 (Lei et al. (2013), World J. Gastroenterol., 19:5138-5143); G207, 1716; NV1020; NV12023; NV1034 and NV1042 (Vargehes et al. (2002), Cancer Gene Ther., 9(12):967-978).

Also included are TIMPs. TIMPs are endogenous tissue inhibitors of metalloproteinases (TIMPs) and are important in many natural processes. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003, the disclosure of which is incorporated by reference herein. Description of TIMP mutations can be found in U.S. Publication No. 2014/0274874 and PCT Publication No. WO 2014/152012.

Also included are antagonistic antibodies for human calcitonin gene-related peptide (CGRP) receptor and bispecific antibody molecule that target the CGRP receptor and other headache targets. Further information concerning these molecules can be found in PCT Application No. WO 2010/075238.

Additionally, bispecific T cell engager (BiTE®) antibodies, e.g. BLINCYTO® (blinatumomab), can be used in the device. Alternatively, included can be an APJ large molecule agonist e.g., apelin or analogues thereof in the device. Information relating to such molecules can be found in PCT Publication No. WO 2014/099984.

In certain embodiments, the medicament comprises a therapeutically effective amount of an anti-thymic stromal lymphopoietin (TSLP) or TSLP receptor antibody. Examples of anti-TSLP antibodies that may be used in such embodiments include, but are not limited to, those described in U.S. Pat. Nos. 7,982,016, and 8,232,372, and U.S. Publication No. 2009/0186022. Examples of anti-TSLP receptor antibodies include, but are not limited to, those described in U.S. Pat. No. 8,101,182. In particularly preferred embodiments, the medicament comprises a therapeutically effective amount of the anti-TSLP antibody designated as A5 within U.S. Pat. No. 7,982,016.

What is claimed is:

1. A testing assembly for a drug delivery device, the testing assembly comprising:
a pressure vessel having a sealed pressure chamber configured to be pressurized to a predetermined pressure and defining an injection opening extending from an exterior thereof to the pressure chamber;
a pierceable barrier extending over and sealing the injection opening;
a measurement device disposed within the pressure chamber; and
a container aligned with the injection opening, such that the container is configured to collect a dose of a drug delivered via a drug delivery device through the pierceable barrier, the measurement device configured to measure the dose of the drug.

2. The testing assembly of claim 1, wherein the container further includes measurement unit markings thereon to provide a visual indication of a volume of the dose.

3. The testing assembly of claim 1, further comprising a device housing configured to securely couple to the drug delivery device and configured to couple to the pressure vessel to thereby orient the drug delivery device adjacent to the injection opening.

4. The testing assembly of claim 3, wherein the pressure vessel further comprises a cap carrying the pierceable barrier therein, and the device housing includes a recess having a shape complementary to the cap such that the device housing is configured to receive the cap within the recess thereof to mount the drug delivery device adjacent to the pierceable barrier.

5. The testing assembly of claim 3, wherein the device housing further comprises a positioning member configured to engage and position the drug delivery device within the device housing to align the delivery structure with the pierceable barrier when the device housing is coupled to the pressure vessel.

6. The testing assembly of claim 3, further comprising a base plate configured to have the drug delivery device adhesively mounted thereto, wherein the device housing is configured to removably receive the base plate to thereby restrict movement of the device in at least one direction.

7. The testing assembly of claim 1, further comprising an actuation force test assembly configured to engage an activation switch on the drug delivery device to determine a force required for actuation thereof.

8. The testing assembly of claim 7, wherein the actuation force test assembly comprises a drive mechanism, a mount, and a force sensor, wherein the force sensor is coupled to a forward portion of the mount and the mount is configured to be driven by the drive mechanism so that the force sensor engages and actuates the activation switch of the drug delivery device.

9. The testing assembly of claim 8, wherein the drive mechanism comprises a motor and the actuation force test assembly further includes a drive shaft configured to be rotated by the motor.

10. The testing assembly of claim 1, further comprising a control circuit in communication with the measurement device and configured to determine a dispense time for the drug delivery device based at least in part on changes in the measurement of the dose of the drug measured by the measurement device.

11. The testing assembly of claim 10, further comprising a sensor configured to activate a timer upon actuation of an activation switch of the drug delivery device.

12. The testing assembly of claim 1, wherein the measurement device comprises (a) a scale configured to measure a weight of the dose of the drug, (b) a float sensor, (c) a flow rate sensor, or (d) an optical sensor.

13. A method for testing the operation of a drug delivery device having a delivery mechanism including delivery structure, the method comprising:
pressurizing a pressure chamber within a pressure vessel to simulate back pressure created when subcutaneously delivering a drug to a patient;
operating the drug delivery device so that the delivery structure pierces a pierceable barrier extending over an injection opening of the pressure vessel;
delivering a dose of drug through the delivery structure into the pressure chamber;
collecting the dose within a container disposed within the pressure chamber; and
measuring the dose collected with a measurement device.

14. The method of claim 13, wherein measuring the dose comprises measuring a weight of the dose using a scale disposed within the pressure chamber.

15. The method of claim 13, further comprising determining a dispense time for the dose based at least in part on weight measurement changes.

16. The method of claim 13, further comprising determining an actuation force required to actuate an activation switch of the drug delivery device.

17. The method of claim 16, wherein determining the actuation force comprises driving a force sensor into engagement with the activation switch, wherein driving the force sensor into engagement with the activation switch further comprises starting a timer in response to a signal from a sensor to determine a dispense time for the dose.

18. The method of claim 13, further comprising:
mounting the drug delivery device to a base plate; and
securing the drug delivery device within a device housing;
mounting the device housing to the pressure vessel so that the drug delivery device is aligned with the pierceable barrier.

19. The method of claim 18, further comprising determining a removal force required to remove the drug delivery device from the base plate.

20. The method of claim 19, wherein determining the removal force required to remove the drug delivery device from the base plate comprises coupling a force sensor to an end of the drug delivery device and shifting the base plate and force sensor relative to one another in a direction generally orthogonal to the base plate.

* * * * *